United States Patent
Sakaguchi et al.

(10) Patent No.: US 7,145,980 B2
(45) Date of Patent: Dec. 5, 2006

(54) X-RAY DIAGNOSIS APPARATUS AND METHOD FOR OBTAINING AN X-RAY IMAGE

(75) Inventors: Takuya Sakaguchi, Tochigi-ken (JP); Akira Tsukamoto, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 58 days.

(21) Appl. No.: 10/777,640

(22) Filed: Feb. 13, 2004

(65) Prior Publication Data

US 2004/0228442 A1 Nov. 18, 2004

(30) Foreign Application Priority Data

Feb. 13, 2003 (JP) ............... 2003-035569

(51) Int. Cl.
- G01N 23/00 (2006.01)
- G01N 23/201 (2006.01)
- H05G 1/64 (2006.01)

(52) U.S. Cl. ............... 378/7; 378/86; 378/98.4; 378/9

(58) Field of Classification Search ............... 378/7, 378/9, 19, 62, 86, 98.4, 98.5
See application file for complete search history.

(56) References Cited

U.S. PATENT DOCUMENTS

| | | | |
|---|---|---|---|
| 6,748,047 B1 * | 6/2004 | Gonzalez Trotter et al. | 378/62 |
| 6,876,719 B1 * | 4/2005 | Ozaki | 378/7 |
| 2003/0146389 A1 * | 8/2003 | Busse et al. | 250/370.09 |
| 2003/0223539 A1 * | 12/2003 | Granfors et al. | 378/98.8 |

FOREIGN PATENT DOCUMENTS

JP 2000-102529 4/2000

* cited by examiner

Primary Examiner—Courtney Thomas
Assistant Examiner—Irakli Kiknadze
(74) Attorney, Agent, or Firm—Oblon, Spivak, McClelland, Maier & Neustadt, P.C.

(57) ABSTRACT

A method for obtaining an X-ray image for an X-ray diagnosis apparatus including plurality of imaging systems, including: collecting first scatter data using a first X-ray detector after an X-ray is irradiated from a first X-ray tube in a first imaging system; collecting second scatter data using a second X-ray detector after an X-ray is irradiated from a second X-ray tube in a second imaging system; collecting first image data including a scatter component using X-ray detectors after an X-ray is irradiated from a third X-ray tube in the first imaging system; collecting second image data including a scatter component using X-ray detectors after an X-ray is irradiated from a fourth X-ray tube in the second imaging system; and obtaining X-ray images for the first and second imaging systems by subtracting the first and second scatter data from the first and second image data including a scatter component, respectively.

17 Claims, 24 Drawing Sheets

X-RAY DIAGNOSIS APPARATUS AND METHOD FOR OBTAINING AN X-RAY IMAGE

CROSS-REFERENCE TO RELATED APPLICATIONS

This application is based upon and claims the benefit of priority from prior Japanese Patent Application No. 2003-35569 filed on Feb. 13, 2003, the entire contents of which are incorporated herein by reference.

FIELD OF THE INVENTION

The present invention relates generally to an X-ray diagnosis apparatus including a plurality of imaging systems and a method for obtaining an X-ray image.

BACKGROUND OF THE INVENTION

As shown in FIG. 1, a biplane X-ray imaging apparatus (mainly developed for cardio vascular inspection) has two imaging systems to perform imaging from two directions simultaneously. One imaging system has a front imaging system 1 including an X-ray tube 3 and an X-ray detector 4 for obtaining an image of a patient on a plate of a bed from a front side. The other imaging system has a lateral imaging system 2 including an X-ray tube 5 and an X-ray detector 6 for imaging the patient from a lateral-side.

In the biplane X-ray imaging apparatus, the X-rays generated from the X-ray tube 3 of the front imaging system 1 pass through the patient P to directly enter the X-ray detector 4, and also reflect to enter the X-ray detector 6 as scattered X-rays. Similarly, the X-rays generated from the X-ray tube 5 of the front imaging system 2 pass through the patient P to enter the X-ray detector 6, and also reflect inside the patient P to enter the X-ray detector 4 as scattered X-rays.

Therefore, in an imaging sequence, as shown in FIG. 2 and FIGS. 3A–3D, when the X-rays are generated from the X-ray tube 3 of the front imaging system 1 and a signal is read out from the X-ray detector 4 of the front imaging system 1, a signal is read out from the X-ray detector 6 of the lateral imaging system 2 to remove an electric charge generated by the scattered X-rays. After the signal is read out, when the X-rays are generated by the X-ray tube 5 of the lateral imaging system 2 and a signal is read from the X-ray detector 6 of the lateral imaging system 2, a signal is read out from the X-ray detector 4 of the front imaging system 1 to remove an electric charge generated by the scattered X-rays.

Although the influence of each of the scattered X-rays between the front imaging system 1 and lateral imaging system 2 can be removed by the above-mentioned method, the imaging is performed by a double cycle of the minimum cycle of each X-ray detector. That is, an effective frame rate (the number of the frames per unit time) decreases to half of the maximum speed.

As a non-limiting example, it is conceptually desirable that a cardiac imaging is simultaneously performed from the front and lateral sides. However, since the imaging of the front imaging system 1 and the lateral imaging system 2 are performed in turn at a fixed cycle to avoid the influence of the scattered X-rays, the time gap between the front and lateral sides still remains.

In addition, a biplane X-ray diagnosis apparatus is described in Japanese Patent Publication (Kokai) No. 2000-102529.

SUMMARY OF THE INVENTION

Objects of the present invention include: to reduce the influence of scattered X-rays, to improve the frame rate, and to reduce the time gap between front imaging and lateral imaging.

According to one aspect of the invention, method for obtaining an X-ray image for an X-ray diagnosis apparatus including plurality of imaging systems is provided, the method including: collecting first scatter data using a first X-ray detector after at least one X-ray is irradiated from a first X-ray tube in a first imaging system; collecting second scatter data using a second X-ray detector after at least one X-ray is irradiated from a second X-ray tube in a second imaging system; collecting first image data including a scatter component using a plurality of X-ray detectors after at least one X-ray is irradiated from a third X-ray tube in the first imaging system; collecting second image data including a scatter component using a plurality of X-ray detectors after at least one X-ray is irradiated from a fourth X-ray tube in the second imaging system; and obtaining X-ray images for the first and the second imaging systems by subtracting the first and second scatter data from the first and second image data including a scatter component, respectively.

According to another aspect of the invention, a method for obtaining an X-ray image using an X-ray diagnosis apparatus including a first imaging system including a first X-ray tube and a first X-ray detector and a second imaging system including a second X-ray tube and a second X-ray detector is provided, the method including: collecting scatter data using the second X-ray detector after at least one X-ray is irradiated from the first X-ray tube; collecting scatter data using the first X-ray detector after at least one X-ray is irradiated from the second X-ray tube and subsequently collecting the scatter data using the second X-ray detector; collecting, substantially simultaneously, image data including a scatter component using the first and the second X-ray detectors; and obtaining X-ray images imaged using the first imaging system and the second imaging system by subtracting the scatter data collected by the first and second X-ray detectors from the image data including the scatter component collected by the first and second X-ray detectors, wherein a collection time of the scatter data is shorter than a collection time of the image data including the scatter component.

Another non-limiting aspect of the invention includes a method for obtaining an X-ray image using an X-ray diagnosis apparatus including a first imaging system including a first X-ray tube and a first X-ray detector and a second imaging system including a second X-ray tube and a second X-ray detector, the method including: collecting, substantially simultaneously, scatter data using the first and second X-ray detectors after at least one X-ray is irradiated from the first X-ray tube; collecting, substantially simultaneously, image data including a scatter component using the first and the second X-ray detectors after at least one X-ray is irradiated from the second X-ray tube; and obtaining X-ray images imaged using the first imaging system and the second imaging system by subtracting the scatter data collected by the first and second X-ray detectors from the image data including the scatter component collected by the first and second X-ray detectors, wherein a collection time of the scatter data is shorter than a collection time of the image data including the scatter component.

Another non-limiting aspect of the invention includes a method for obtaining an X-ray image using an X-ray diagnosis apparatus including a first imaging system including a first X-ray tube and a first X-ray detector and a second imaging system including a second X-ray tube and a second X-ray detector, the method including: collecting, substantially simultaneously, first scatter data using the first and second X-ray detectors after at least one X-ray is irradiated from the first X-ray tube; collecting second scatter data using the first X-ray detector after at least one X-ray is irradiated from the second X-ray tube and subsequently collecting the second scatter data using the second X-ray detector, subsequently collecting, substantially simultaneously, image data including a scatter component using the first and second X-ray detectors; subtracting the second scatter data from the first scatter data, thereby obtaining subtracted scatter data; obtaining an X-ray image by subtracting the subtracted scatter data from the image data including the scatter component collected by the first X-ray detector; and obtaining an X-ray image by subtracting the scatter data collected by the second X-ray detector from the image data including the scatter component collected by the second X-ray detector, wherein a collection time of the scatter data is shorter than a collection time of the image data including the scatter component.

An X-ray diagnosis apparatus according to another aspect of the invention includes: a plurality of X-ray tubes; and a plurality of X-ray detectors corresponding to respective X-ray tubes, wherein each of the plurality of X-ray detectors includes a first image data collection function for collecting image data using a first number of detection elements and a second image data collection function for collecting image data by a second number of detection elements, the second number being fewer than the first number.

Another aspect of the invention provides a method for obtaining X-ray image by an X-ray diagnosis apparatus including a first X-ray tube configured to irradiate X-rays in a first direction, a first X-ray detector corresponding to the first X-ray tube, a second X-ray tube for irradiating X-rays in a second direction different from the first direction, and a second X-ray detector corresponding to the second X-ray tube, the method including: collecting first image data using the second X-ray detector based on at least one X-ray irradiated from the first X-ray tube; collecting second image data using the first X-ray detector based on at least one X-ray irradiated from the second X-ray tube; collecting third image data at a speed lower than a collecting speed of the second image data using the first X-ray detector based on the X-rays irradiated from the first and second X-ray tubes; collecting at a speed lower than a collecting speed of the first image data fourth image data using the second X-ray detector, substantially simultaneously with the collecting the third image data, based on the X-rays irradiated from the first and second X-ray tubes; removing a scatter component included in the third image data using the second image data; and removing a scatter component included in the fourth image data using the first image data.

Another aspect of the invention provides a method for obtaining an X-ray image using an X-ray diagnosis apparatus including a first X-ray tube configured to irradiate X-rays in a first direction, a first X-ray detector corresponding to the first X-ray tube, a second X-ray tube for irradiating X-rays in a second direction different from the first direction, and a second X-ray detector corresponding to the second X-ray tube, the method including: collecting first image data using the second X-ray detector based on at least one X-ray irradiated from the first X-ray tube; collecting second image data using the first X-ray detector based on the at least one X-ray irradiated from the first X-ray tube; collecting third image data using the first X-ray detector based on X-rays irradiated from the first and second X-ray tubes; collecting fourth image data using the second X-ray detector, substantially simultaneously to collecting the third image data, based on the X-rays irradiated from the first and second X-ray tubes; removing a scatter component included in the third image data using the second image data; and removing a scatter component included in the fourth image data using the first image data.

Another non-limiting aspect of the invention includes a method for obtaining an X-ray image using an X-ray diagnosis apparatus including a first X-ray tube configured to irradiate X-rays in a first direction, a first X-ray detector corresponding to the first X-ray tube, a second X-ray tube configured to irradiate X-rays in a second direction different from the first direction, and a second X-ray detector corresponding to the second X-ray tube, the method including: irradiating at least one X-ray from the first X-ray tube; collecting first image data using the second X-ray detector based on the at least one X-ray irradiated from the first X-ray tube; irradiating at least one X-ray from the second X-ray tube; collecting second image data using the second X-ray detector based on the X-rays irradiated from the first and second X-ray tubes at a lower speed than a collecting speed of the first image data; and removing a scatter component included in the second image data using the first image data.

Another aspect of the present invention includes an X-ray diagnosis apparatus, including: a first X-ray tube configured to irradiate X-rays in a first direction; a first X-ray detector corresponding to the first X-ray tube; a second X-ray tube configured to irradiate X-rays in a second direction different from the first direction; a second X-ray detector corresponding to the second X-ray tube; a controller configured to control the second X-ray detector to collect first image data based on at least one X-ray irradiated from the first X-ray tube, the first X-ray detector to collect second image data based on at least one X-ray irradiated from the second X-ray tube; the first X-ray detector to collect third image data based on the X-rays irradiated from the first and second X-ray tubes at a lower speed than a collecting speed of the second image data, the second X-ray detector to collect fourth image data, substantially simultaneously to collecting the third image data, based on the X-rays irradiated from the first and second X-ray tubes at a lower speed than a collecting speed of the first image data; and an image processor configured to remove a scatter component included in the third image data using the second image data and to remove a scatter component included in the fourth image data using the first image data.

Another non-limiting aspect of the present invention includes an X-ray diagnosis apparatus, including: a first X-ray tube configured to irradiate X-rays in a first direction; a first X-ray detector corresponding to the first X-ray tube; a second X-ray tube configured to irradiate X-rays in a second direction that is different from the first direction; a second X-ray detector corresponding to the second X-ray tube; a controller configured to control the second X-ray detector to collect first image data based on at least one X-ray irradiated from the first X-ray tube, the first X-ray detector to collect second image data based on at least one X-ray irradiated from the first X-ray tube, the first X-ray detector to collect third image data based on the X-rays irradiated from the first and second X-ray tubes, the second X-ray detector to collect fourth image data, substantially simultaneously to collecting the third image data, based on the X-rays irradiated from the first and second X-ray tubes; and an image processor configured to remove a scatter component included in the third image data by using the second image data and to remove a scatter component included in the fourth image data using the first image data.

Another non-limiting aspect of the invention provides an X-ray diagnosis apparatus including: a first X-ray tube configured to irradiate X-rays in a first direction; a first X-ray detector corresponding to the first X-ray tube; a second X-ray tube configured to irradiate X-rays in a second direction different from the first direction; a second X-ray detector corresponding to the second X-ray tube; a controller configured to control the first X-ray tube to irradiate at least one X-ray, the second X-ray detector to collect first image data based on the at least one X-ray irradiated from the first X-ray tube, the second X-ray tube to irradiate at least one X-ray, and the second X-ray detector to collect second image data based on the X-rays irradiated from the first and second X-ray tubes at a lower speed than a collecting speed of the first image data; and an image processor configured to remove a scatter component included in the second image data using the first image data.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings. In the drawings.

DETAILED DESCRIPTION OF EXEMPLARY EMBODIMENTS OF THE INVENTION

Figure 1:
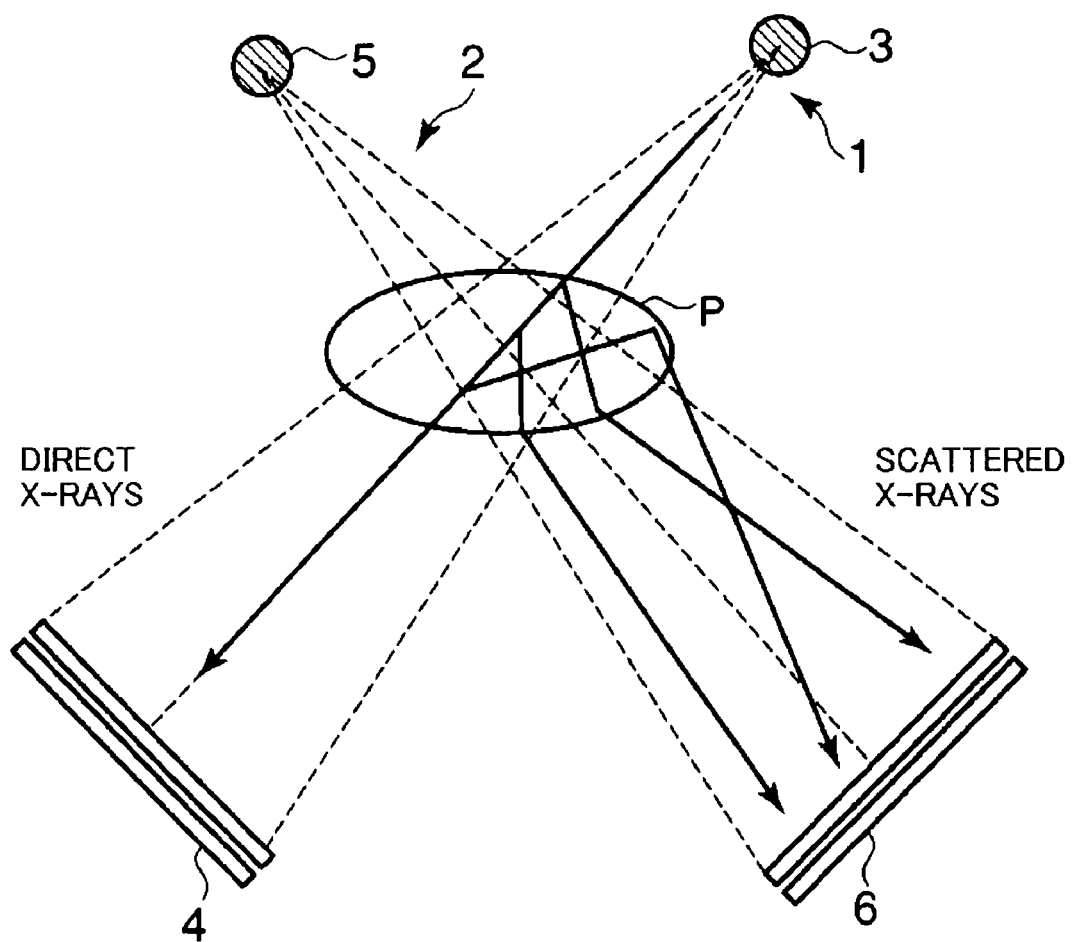
FIG. 1 is an illustration for explaining scattered X-rays.
Figure 2:
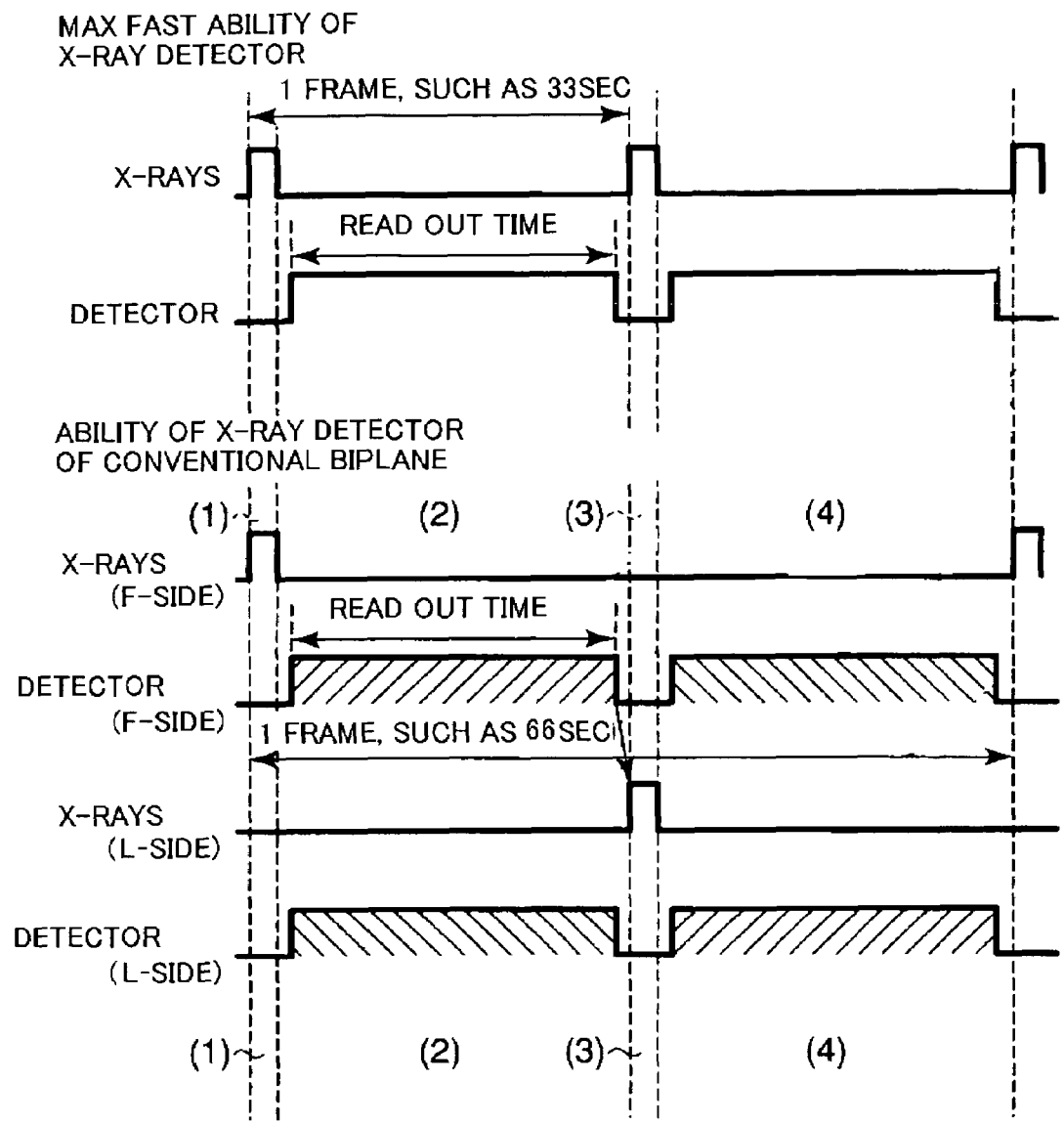
FIG. 2 is an illustration for explaining a conventional imaging sequence.
Figures 3A, 3B, 3C, 3D:
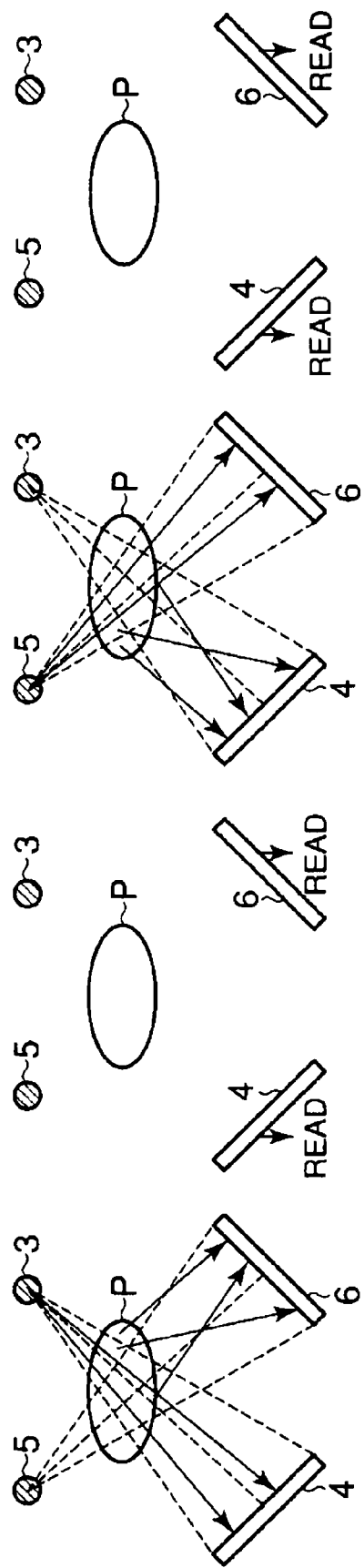
FIG. 3A through 3D are illustrations for explaining scattered X-rays.
Figure 4:
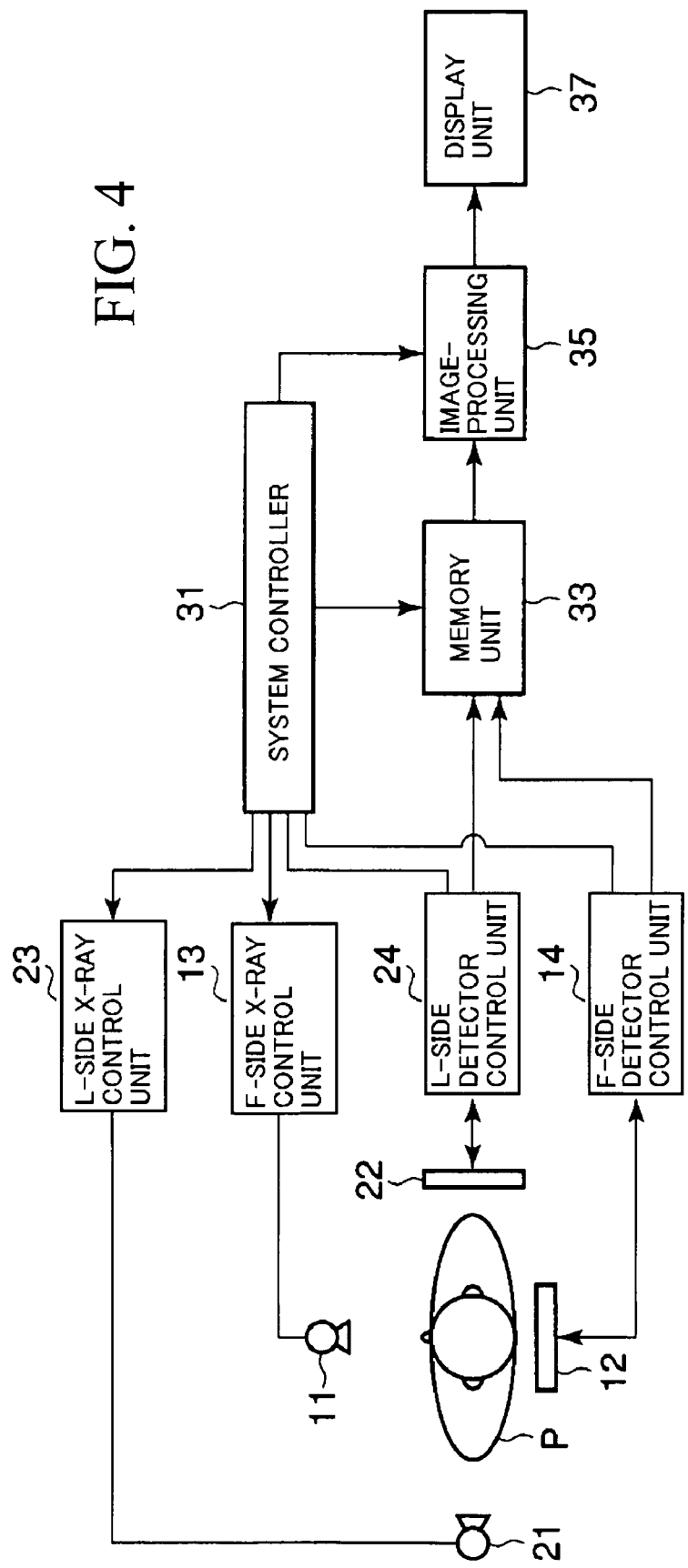
FIG. 4 is a block diagram of an X-ray diagnosis apparatus of a non-limiting embodiment.

With reference to the drawings, a non-limiting embodiment of a biplane X-ray imaging method and a biplane X-ray imaging apparatus is explained. FIG. 4 shows a block diagram of the biplane X-ray imaging apparatus. The biplane X-ray imaging apparatus includes two or more X-ray imaging systems, for example, a front imaging system (F), and a lateral imaging system (L). The front imaging system F has an X-ray tube 11 and an X-ray detector 12 positioned opposite the X-ray tube 11. A patient is positioned between the X-ray tube 11 and the X-ray detector 12. The lateral imaging system L has an X-ray tube 21 and an X-ray detector 22 positioned opposite the X-ray tube 21. A patient is positioned between the X-ray tube 21 and the X-ray detector 22.

The X-ray detectors 12 and 22 may be solid flat detectors including a plurality of detection elements (pixels) that change incident X-rays into an electric charge directly or indirectly and are 2-dimensionally arranged, for example. The X-ray tube 11 of the front imaging system is attached in one end of a C-arm located on the floor (not shown), and the X-ray detector 12 is attached in the other end of the C-arm. The X-ray tube 21 of the lateral imaging system is attached in one end of an Ω-arm hung from a ceiling (not shown), and the X-ray detector 22 is attached in the other end of the Ω-arm. A supporting machine of the C-arm and a supporting machine of the Ω-arm are designed so that an imaging center axis which connects a detection center of the X-ray detector 12 to a focus of the X-ray tube 11 crosses an imaging center axis which connects a detection center of the X-ray detector 22 to a focus of the X-ray tube 21 at the so-called isocenter.

An F-side X-ray control unit 13 is connected to the X-ray tube 11 of the front imaging system. The F-side X-ray control unit 13 applies a high voltage between a cathode and a rotation anode of the X-ray tube 11. Moreover, the F-side X-ray control unit 13 supplies heating current to a cathode filament of the X-ray tube 11. A heat electron emitted from the heated filament collides with a target of the rotation anode. Thereby, the X-rays are generated. An L-side X-ray control unit 23 is connected to the X-ray tube 21 of the lateral imaging system. The L-side X-ray control unit 23 applies a high voltage between a cathode and a rotation anode of the X-ray tube 21. Moreover, the L-side X-ray control unit 23 supplies heating current to the cathode filament of the X-ray tube 21. An F-side detector control unit 14 is connected to the X-ray detector 12 of the front imaging system. The F-side detector control unit 14 controls data read out from the F-side X-ray detector 12. An L-side detector control unit 24 is connected to the X-ray detector 22 of the lateral imaging system. The L-side detector control unit 24 controls data read out from the L-side X-ray detector 22.

A system controller 31 controls each operation of the F-side X-ray control unit 13, the F-side detector control unit 14, the L-side X-ray control unit 23, and the L-side detector control unit 24 to perform an imaging operation, and controls a memory unit 33, an image-processing unit 35 and a display unit 37 according to the imaging operation.

Figure 5:
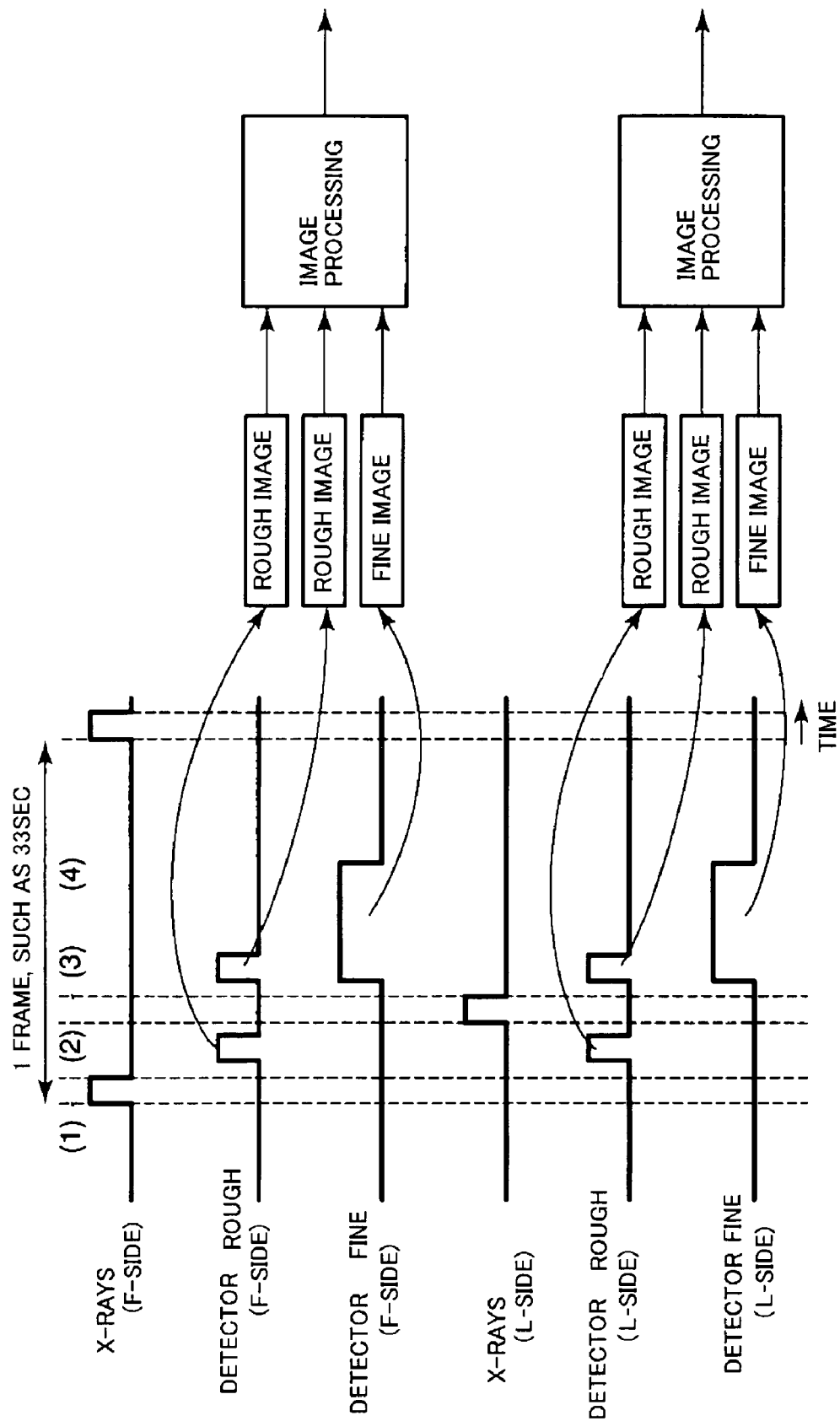
FIG. 5 is an illustration for explaining an imaging sequence according to the embodiment.
Figure 6:
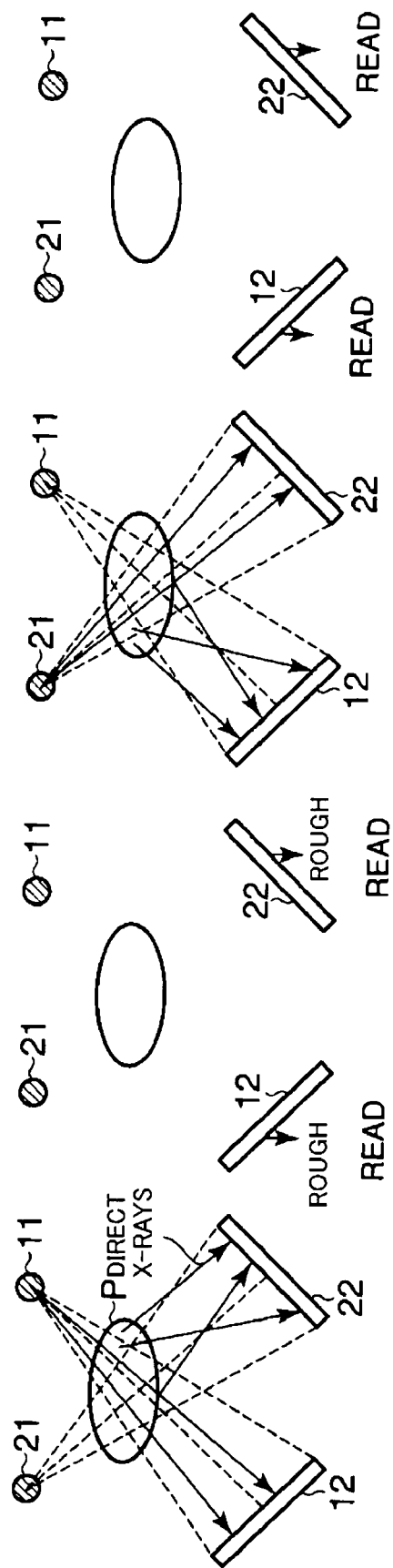
FIG. 6A through 6D are illustrations for explaining a scattered X-rays according to the embodiment.
Figure 7:
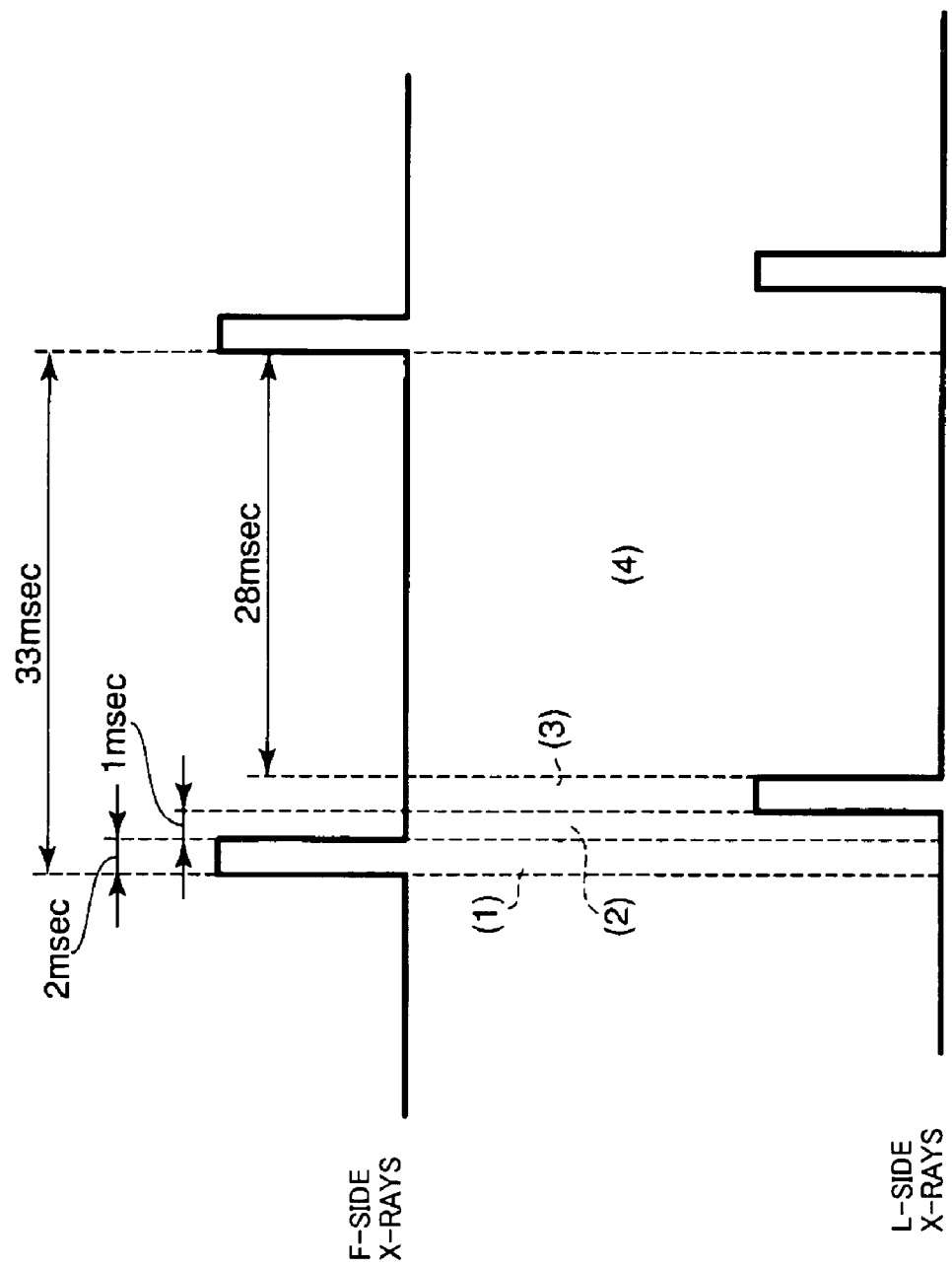
FIG. 7 is an illustration for explaining an exemplary part of the imaging sequence of FIG. 5.

An exemplary imaging sequence of the embodiment is shown in FIG. 5, FIG. 6, and FIG. 7. The imaging sequence is divided into four terms. In term (1), the X-rays are generated from the F-side X-ray tube 11, and in the next term (2), rough (low spatial resolution) image data is read from the X-ray detectors 12 and 22 of both the F and the L sides at high speed. In term (3), the X-rays are generated from the L-side X-ray tube 21, and in term (4), rough image data is almost simultaneously read from the X-ray detectors 12 and 22 of both F and L sides at high speed, and fine (high spatial resolution) image data is almost simultaneously read from the X-ray detectors 12 and 22 of both F and L sides at low speed.

In the non-limiting embodiment, three kinds of image data are acquired in the F-side imaging system and the L-side imaging system, respectively. The three kinds image data contain different signal components and different scatter components, respectively. When image processing is performed on at least two types of image data among the three types of image data, the scatter components of the F-side and L-side imaging systems are removed, and fine image data that mainly includes the signal components is obtained.

Thus, in term (4) the F-side and L-side data read out is performed in parallel. Therefore, cycle time can be shortened and a frame rate can be reduced in comparison with serial data read out from the L and F-sides. Moreover, although it is useful to read out the scatter component to remove the scatter component from each image, in the embodiment, the influence caused by the read out operation of the scatter component to the cycle time can be reduced by reading out the scatter component at low resolution and at high speed (short time), considering that spatial frequency of the scatter component is low. Furthermore, by reading out the scatter component at low resolution and at high speed, term (2) can be shortened and a gap for imaging time between the F-side and the L-side can be shortened.

The above-mentioned imaging sequence is an exemplary imaging sequence, and there are many variations by combining a read out format of the X-ray detector, a structure of the X-ray detector, and image-processing format. Read out formats include an electric charge read out format and a voltage read out format. Each format can be applied in the embodiment. Since the electric charge in a pixel capacitor remains after the data is read out in the voltage read out format, a flush operation is necessary to reset the pixel capacitor. Options for timing of the flush operation include: a flush every read out type and a flush every frame. Structures of the X-ray detector include: a two-layer type, a partial read out type (a single layer, independent signal line), and a partial read out type (a single layer, common signal line), for example. Moreover, image processing formats include: spatial correction, reuse reconstruction, low resolution conversion, and modified algorithm low resolution conversion. There are many possible variations of the imaging sequence by combining the above-mentioned options, as well as variations that will be apparent to one of ordinary skill in the art. Some non-limiting combinations include the following:

(1-1) Electric charge read out format+Two layer type, (1-2) Electric charge read out format+Partial read out type (a single layer, independent signal line)+Spatial correction, (1-3) Electric charge read out format+Partial read out type (a single layer, common signal line)+Spatial correction, (2-1) Electric charge read out format+Partial read out type (a single layer, independent signal line)+Reuse reconstruction, (2-2) Electric charge read out format+Partial read out type (a single layer, common signal line)+Reuse reconstruction, (3-1) Voltage read out format+Flush every read out type+Two layer type, (3-2) Voltage read out format+Flush every read out type+Partial read out type (a single layer, independent signal line)+Spatial correction, (3-3) Voltage read out format+Flush every read out type+Partial read out type (a single layer, common signal line)+Spatial correction, (4-1) Voltage read out format+Flush every read out type+Partial read out type (a single layer, independent signal line)+Reuse reconstruction, (4-2) Voltage read out format+Flush every read out type+Partial read out type (a single layer, common signal line)+Reuse reconstruction, (5-1) Voltage read out format+Flush every frame type+Two layer type, (5-2) Voltage read out format+Flush every frame type+Partial read out type (a single layer, independent signal line)+Spatial correction, (5-3) Voltage read out format+Flush every frame type+Partial read out type (a single layer, common signal line)+Spatial correction, (6-1) Voltage read out format+Flush every frame type+Two layer type+Low resolution conversion, (6-2) Voltage read out format+Flush every frame type+Partial read out type (a single layer, independent signal line)+Spatial correction+Low resolution conversion, (6-3) Voltage read out format+Flush every frame type+Partial read out type (a single layer, common signal line)+Spatial correction+Low resolution conversion, (7-1) Voltage read out format+Flush every frame type+Two layer type+Low resolution conversion of modified algorithm, (7-2) Voltage read out format+Flush every frame type+Partial read out type (a single layer, independent signal line)+Spatial correction+Low resolution conversion of modified algorithm, (7-3) Voltage read out format+Flush every frame type+Partial read out type (a single layer, common signal line)+Spatial correction+Low resolution conversion of modified algorithm, (8-1) Voltage read out format+Flush every frame type+Partial read out type (a single layer, independent signal line)+Reuse reconstruction, (8-2) Voltage read out format+Flush every frame type+Partial read out type (a single layer, common signal line)+Reuse reconstruction, (9-1) Voltage read out format+Flush every frame type+Partial read out type (a single layer, independent signal line)+Reuse reconstruction+Low resolution conversion, (9-2) Voltage read out format+Flush every frame type+Partial read out type (a single layer, common signal line)+Reuse reconstruction+Low resolution conversion, (10-1) Voltage read out format+Flush every frame type+Partial read out type (a single layer, independent signal line)+Reuse reconstruction+Low resolution conversion of modified algorithm, and (10-2) Voltage read out format+Flush every frame type+ Partial read out type (a single layer, common signal line)+ Reuse reconstruction+Low resolution conversion of modified algorithm.

The above-mentioned variations are explained below.

(1-1) Electric charge read out format+Two layer type

The electric charge read out format where the electric charge generated by the irradiated X-rays is read out as a current signal is applied to the X-ray detectors 12 and 22. In the electric charge read out format, when the data is read out, the electric charge is removed from the pixel capacitor and the pixel capacitor is reset.

Figure 8:
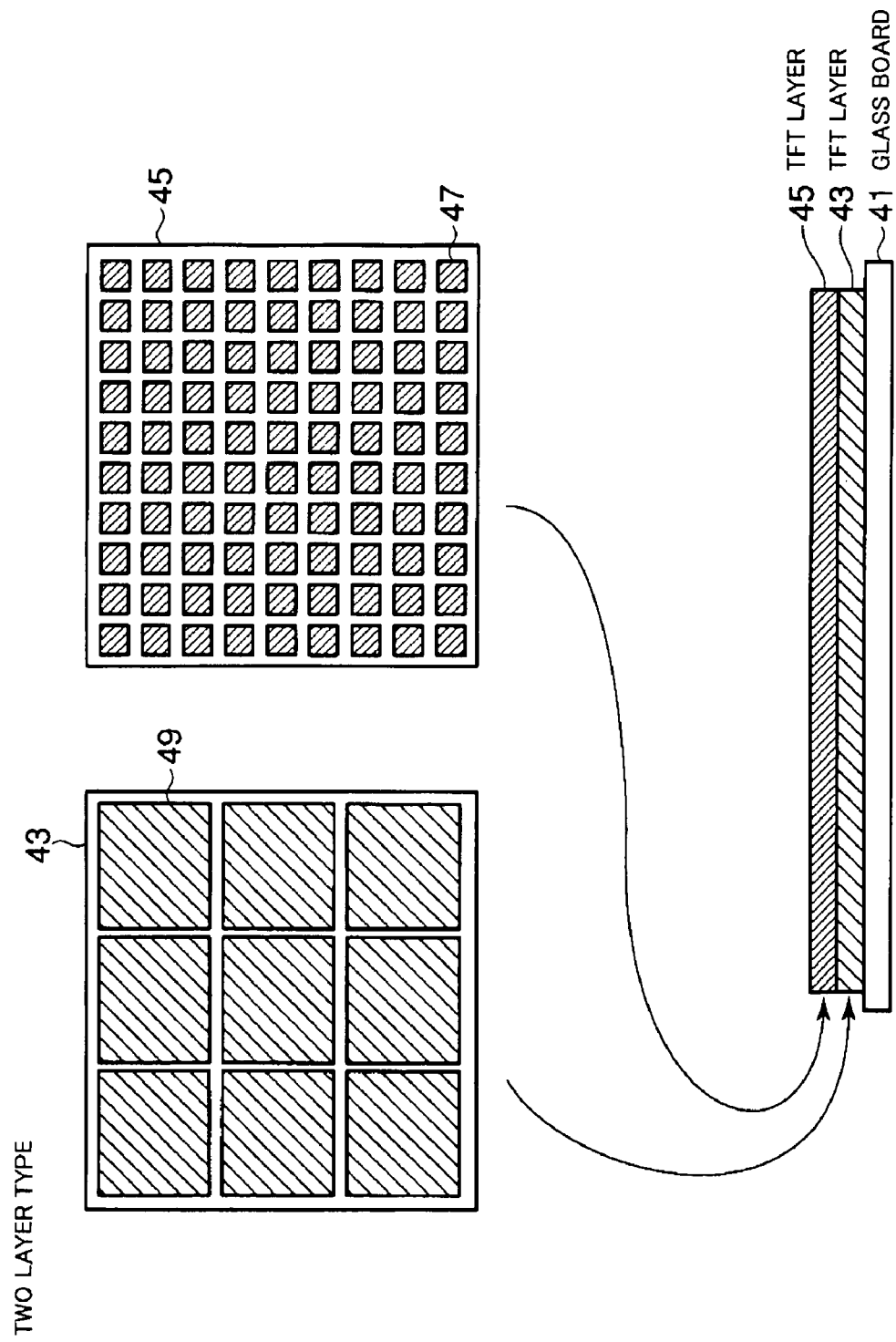
FIG. 8 is an illustration for explaining an example of a two-layer type X-ray detector of FIG. 4.

FIG. 8 shows the X-ray detector 12 of the front imaging system. Since the X-ray detector 22 of the lateral imaging system is the same as or similar to the X-ray detector 12 of the front imaging system, the explanation for the X-ray detector 22 is omitted.

On a glass substrate 41 of the X-ray detector 12, pixel arrangement layers 43 and 45 are piled up as two layers. The first layer 45 is a usual TFT structure where a plurality of detection elements 47 are arranged. The second layer 43 is located between the first layer 45 and the glass substrate 41. Although the number of the detection elements 49 (the number of pixels) of the second layer 43 is fewer than the number of the detection elements 47 of the first layer 45, detection area of the detection elements 49 of the second layer is larger than that of the detection elements 47 of the first layer 45. The detection elements 49 of the second layer 43 are arranged in a region that is almost the same size as the size of the region in which the detection elements 47 of the first layer 45 are arranged. The X-rays that penetrate through the first layer 45 go into the second layer 43. Since the number of pixels of the second layer 43 is fewer than that of the first layer 45, the read out from all pixels of the second layer 43 is completed at higher speed (i.e., faster) than that of the first layer 45.

Figure 9:
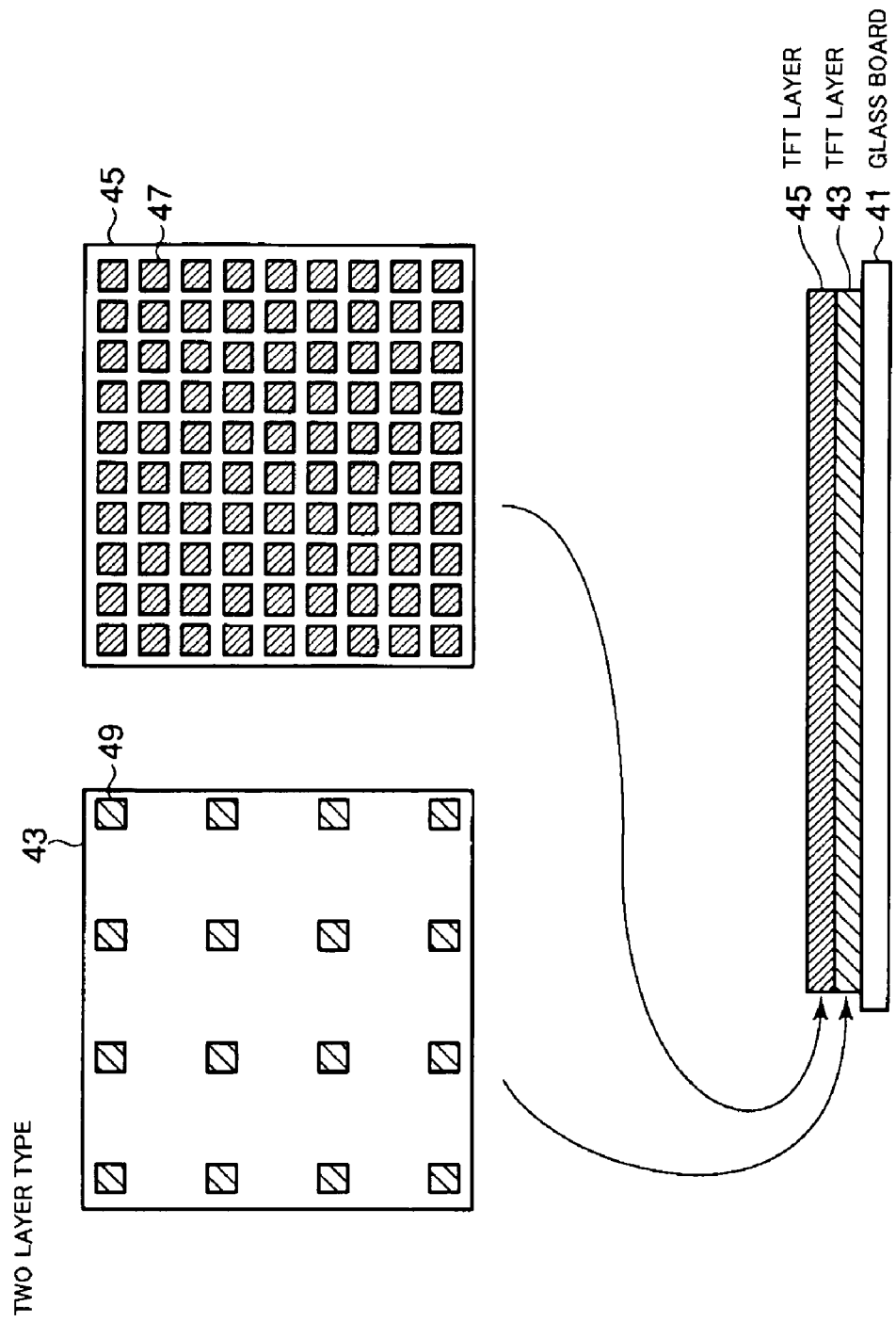
FIG. 9 is an illustration for explaining another example of a two-layer type X-ray detector of FIG. 4.

As shown in FIG. 9, the detection area of the detection elements 49 of the second layer 43 may be almost the same as the detection area of the detection elements 47 of the first layer 45, and the detection elements 49 may be separately arranged in a region that is almost the same size as the region in which the detection elements 47 are arranged.

Figure 10:
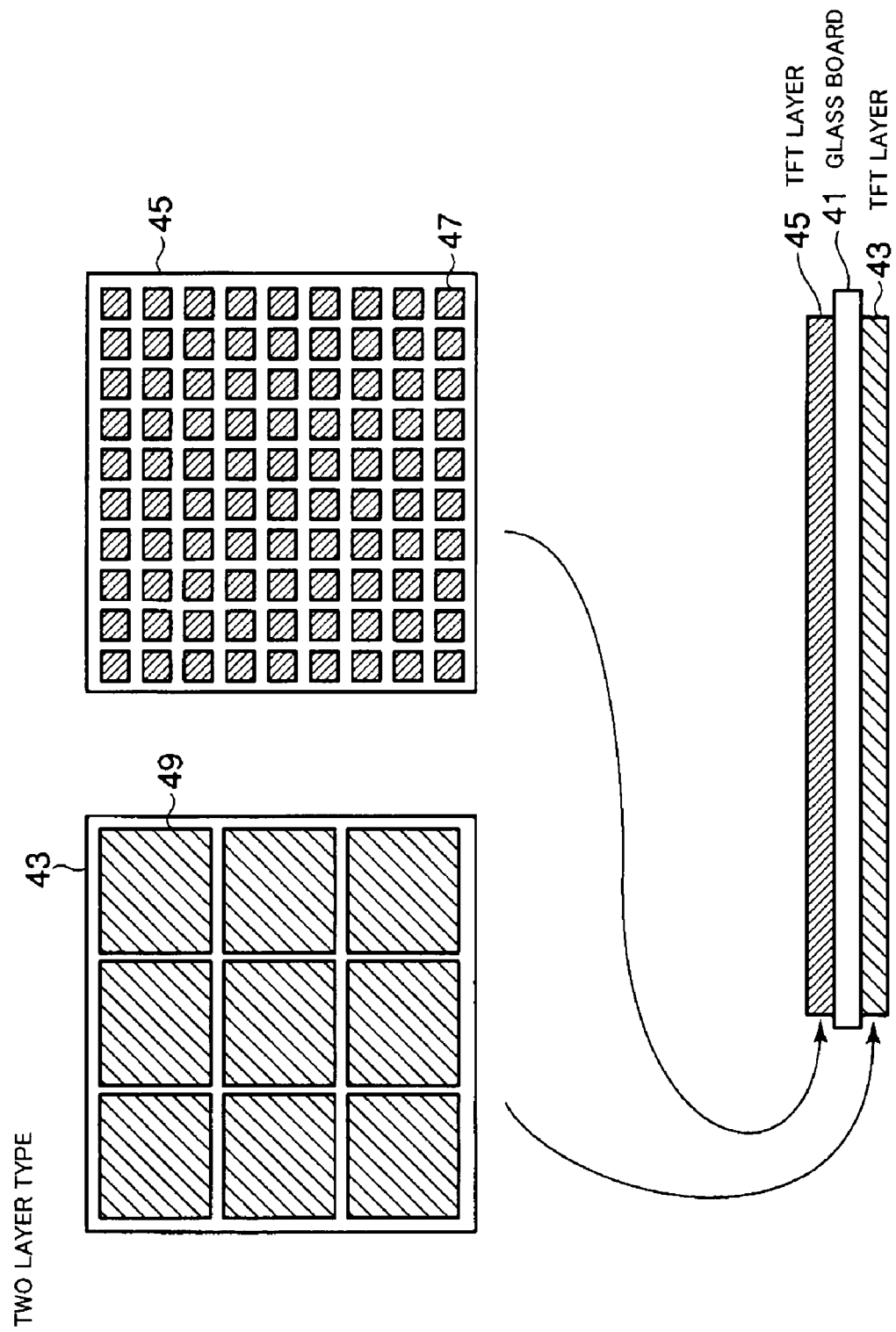
FIG. 10 is an illustration for explaining another example of a two-layer type X-ray detector of FIG. 4.
Figure 11:
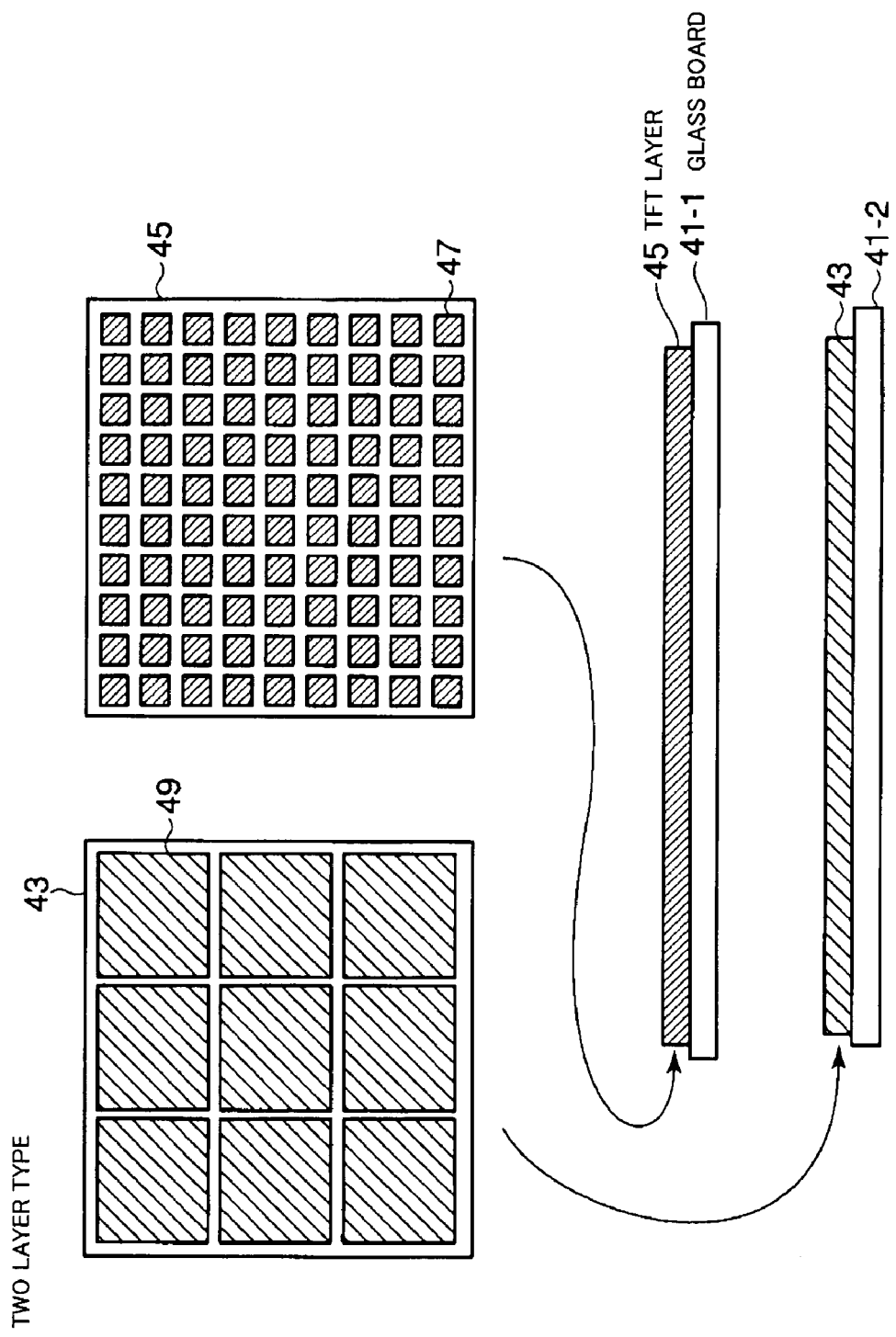
FIG. 11 is an illustration for explaining another example of a two-layer type X-ray detector of FIG. 4.

Alternatively, as shown in FIG. 10, the first layer 45 may be located on a surface of the glass substrate 41, and the second layer 43 may be located on a back face of the glass substrate 41. Alternatively, as shown in FIG. 11, the first layer 45 may be located on a surface of a glass substrate 41-1, the second layer 43 may be located on a surface of a glass substrate 41-2, and the substrates may be stacked. In this case, the glass substrate 41-1 may be bonded to the second layer 43, for example.

Figure 12:
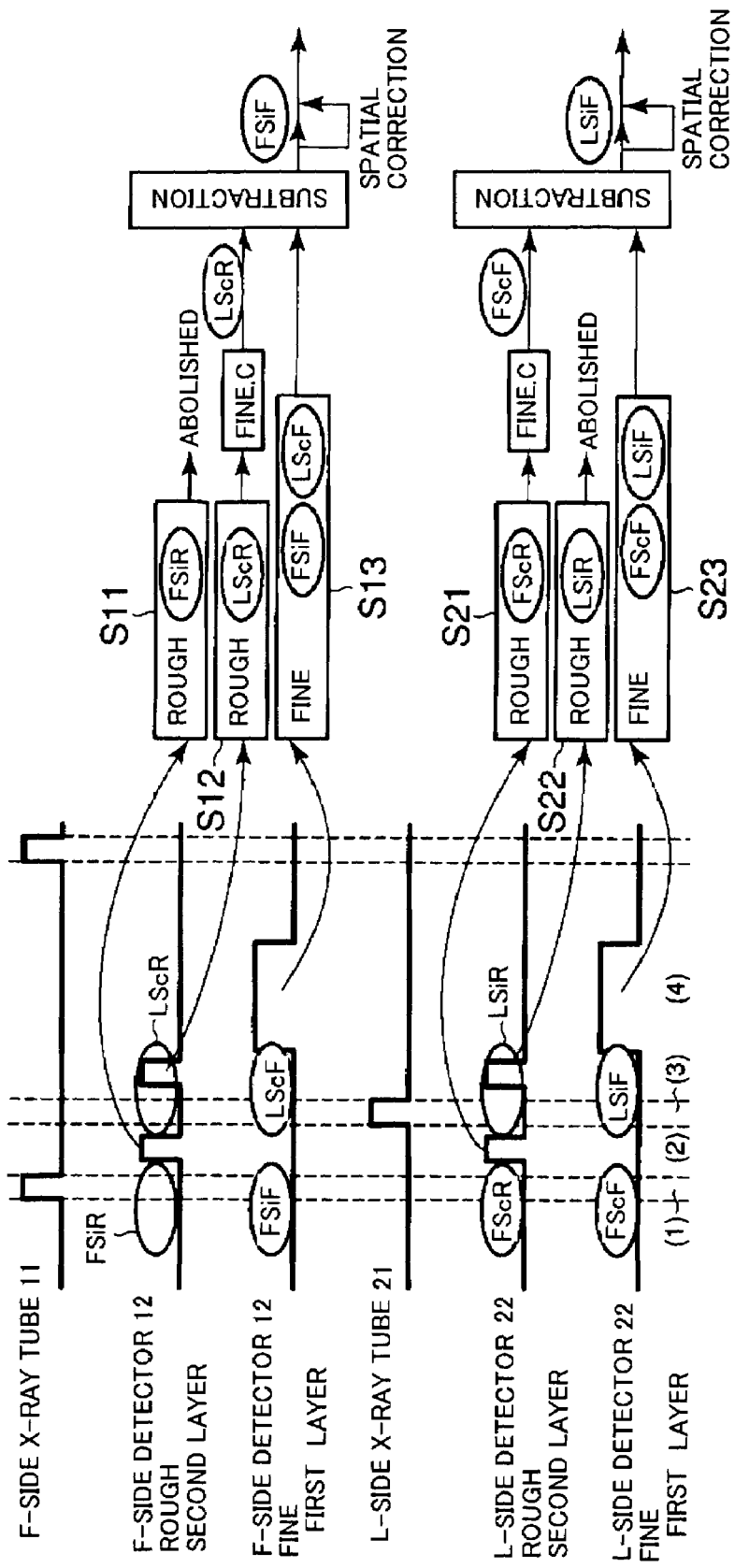
FIG. 12 is an illustration for explaining an imaging sequence and an image processing of each format.

FIG. 12 shows an imaging sequence of one cycle in the (electric charge read out format+Two layer type). In term (1), the X-rays are generated from the F-side X-ray tube 11. In term (1), the direct X-rays from the F-side X-ray tube 11 go through the patient, and are detected as signal components by the first and second layers 45 and 43 of the first of F-side X-ray detector 12. In term (1), the X-rays from the F-side X-ray tube 11 are also scattered inside the patient, and the scattered X-rays are detected as scatter components by the first and second layers of the L-side X-ray detector 22.

In term (2), rough image data S11 is read out from the second layer 43 of the F-side X-ray detector 12 at high speed. The image data S11 includes the direct X-rays (signal component) from the F-side, which is hereinafter referred to as "FSiR." In term (2), rough image data S21 is read out from the second layer of the L-side X-ray detector 22 at high speed in parallel to read out of the rough image data S11 from the second layer 43 of the F-side X-ray detector 12. The image data S21 mainly includes the scatter component caused by the scattered X-ray from the F-side X-ray tube 11, which is hereinafter referred to as "FScR." After the image data S11 and S21 are read out from the second layers of the F-side and L-side X-ray detectors, in term (3), the X-rays are generated from the L-side X-ray tube 21. In term (3), the scattered X-rays among the X-rays from the L-side X-ray tube 21 are detected by first and second layers 45 and 43 of the F-side X-ray detector 21. In term (3), the direct X-rays from the L-side X-ray tube 21 pass through the patient and are detected by the first and second layers of the L-side X-ray detector 22.

In term (4), rough image data S12 is read out from the second layer 43 of the F-side X-ray detector 12. Since the read electric charge is not held in the electric charge read out format, the image data S12 read out in term (4) does not reflect the accumulated electric charge in term (1), but mainly indicates the scatter component caused by the X-rays from L-side and accumulated in term (3), hereafter "LScR." Moreover, in term (4), rough image data 22 is read out from the second layer 43 of the L-side X-ray detector 22 at high speed in parallel to read out of the rough image data S12 from the second layer 43 of the F-side X-ray detector 12. Since the image data S22 read out in term (4) does not reflect the accumulated electric charge in term (1), the image data S22 mainly includes the signal component caused by the direct X-rays from L-side and accumulated in term (3), hereafter "LSiR."

Furthermore, fine image data S13 is read out from the first layer 45 of the F-side X-ray detector 12 at low speed. Since the image data S13 read out from the first layer 45 in term (4) reflects the electric charge accumulated in term (1) and term (3), the image data S13 includes the signal component caused by the direct X-rays from the F-side accumulated in term (1) and the scatter component caused by the X-rays from the L-side accumulated in term (3), which is referred to as "FSiF+LScF." Moreover, fine image data S23 is read out from the first layer of the L-side X-ray detector 22 in term (4) at low speed. Since the image data S23 read out from the first layer in term (4) reflects the electric charge accumulated in term (1) and term (3), the image data S23 includes the scatter component caused by the X-rays from the F-side accumulated in term (1) and the signal component caused by the direct X-rays from the L-side accumulated in term (3), which is referred to as "FScF+LSiF." With the two layer type, although FIG. 12 shows that the data is read out from the first layer and the second layer in turn in term (4), the data is read out from the first layer in parallel to the data read out from the second layer.

The image processing for the image data obtained by the sequence will now be explained. Regarding the F-side, since the fine image data S13 includes the signal component and the scatter component, it is necessary to remove the scatter component. The scatter component is included in the data S12. The scatter component has a lower space frequency than that of the signal component, and even low resolution image data can be used. The low resolution image data S12 is converted to such high resolution image data (fine conversion) as the image data S13, and when subtraction is performed between the converted image data S12 related to the scatter component and the fine image data S13, L-side fine image data where the scatter component is removed can be created.

Similarly, regarding the L-side, the image data S23 obtained in high resolution includes the scatter component caused by the X-rays from the F-side X-ray tube 11. The scatter component is included in the image data S21. The image data S21 is converted to high resolution image data, such as the image data S23, and when a subtraction is performed between the converted image data S21 related to the scatter component and the fine image data S23, fine image data S24 where the scatter component is removed can be created.

As described above, in the embodiment, it is possible to read out the data from the F-side and the L-side in parallel. Therefore, it is possible to improve the frame rate in comparison with the serial data read out from the L-side and the F-side. Moreover, although it is useful to read out the scatter component to remove the scatter component from each image, in the non-limiting embodiment, the influence caused by the read out operation of the scatter component to the cycle time can be reduced by reading out the scatter component at low resolution and at high speed (short time), considering that spatial frequency of the scatter component is low. Furthermore, by reading out the scatter component at low resolution and at high speed, term (2) can be shortened and a gap for imaging time between the F-side and the L-side can be shortened.

(1-2) Electric charge read out format+Partial read out type (a single layer, independent signal line)+Spatial correction In the two layer type as mentioned above, the second layer where the pixels are arranged roughly is separated from the first layer where the pixels are arranged finely. However, in a partial read out type X-ray detector (a single layer, independent signal line), pixels are arranged on a single layer. Rough image data is read out from specific pixels in terms (2) and (4), and fine image data is read out from the pixels other than the specific pixels in term (4).

Figure 13:
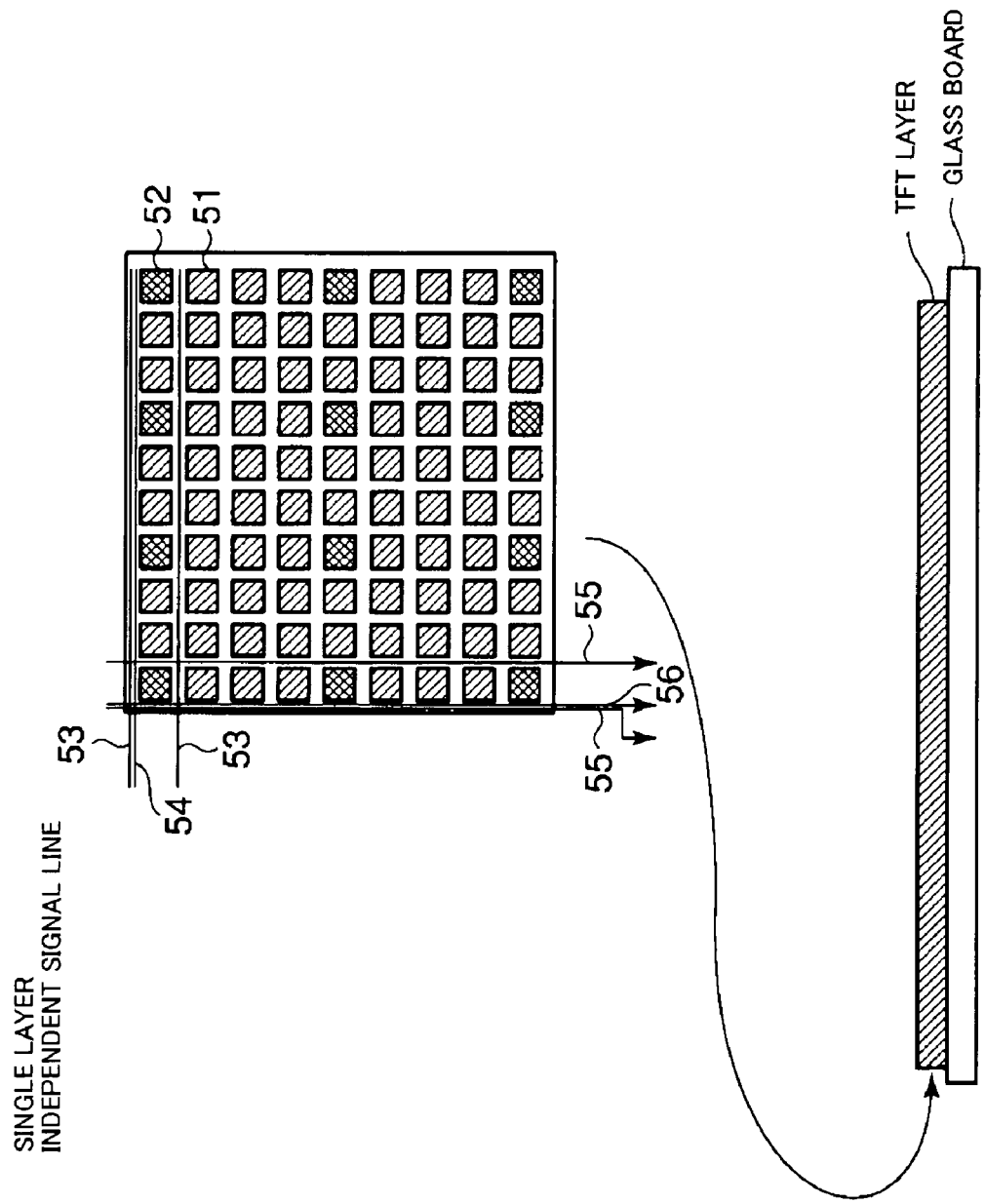
FIG. 13 is an illustration for explaining an example of a one-layer (independent signal line) type X-ray detector of FIG. 4.

FIG. 13 shows the partial read out type X-ray detector (a single layer, independent signal line). The specific pixels shown as a double slash are assigned to read out the rough image data, and the other pixels 51 shown as a single slash are assigned to read out the fine image data. The number of the specific pixels 52 is fewer than the number of the pixels 51. The specific pixels are separately arranged in a lengthwise direction and a crosswise direction such that the pixels 51 are therebetween. The specific pixels 52 in the crosswise direction are connected to a gate line 54 that can drive the specific pixels 52 independently from the pixels 51 driven by a gate line 53. The specific pixels 52 in the lengthwise direction are connected to a signal line 56 that is independent from a signal line 55 of the pixels 51. At high speed read out, the gate lines 54 connected to the specific pixels 52 are activated in turn, and the data is read out via the signal lines 56 connected to the specific pixels in turn.

In term (2) of FIG. 12, the rough image data S11 is read from the specific pixel 52 of the F-side X-ray detector 12 at high speed, and (in parallel) the rough image data S21 is read from the specific pixel 52 of the L-side X-ray detector 22 at high speed. Also in term (4), the rough image data S12 is read from the specific pixel 52 of the F-side X-ray detector 12 at high speed, and (in parallel) the rough image data S22 is read from the specific pixel 52 of L-side X-ray detector 22 at high speed. In the same term (4), the fine image data S113 is read from the other pixels 51 of the F-side X-ray detector 12 at low speed, and in parallel, the fine image data S23 is read from the other pixels 51 of the L-side X-ray detector 22 at low speed. Although it is described in FIG. 12 that the data read out from the specific pixels 52 is performed separately from the data read out from the other pixels 51 in turn, these data read outs are performed in parallel.

Regarding the F-side, the low resolution image data S12 is converted to high resolution image data (fine conversion) such as the image data S13 to remove the scatter component from the high resolution image data 13. When subtraction is performed between the converted image data S12 related to the scatter component and the fine image data S13 including the signal component and the scatter component, L-side fine image data where the scatter component is removed can be created.

Since the partial pixels are applied to the specific pixels 52, signals from the specific pixels 52 are lacking in the image data S13. Since the partial pixels are applied to the specific pixels 52 in the independent partial read out type, signals are lacking that correspond to the specific pixels on the image data. When the image data S13 where a scatter component is removed by subtraction is spatially corrected, the data corresponding to the specific pixels is interpolated.

Similarly, regarding the L-side, in order to remove the scatter component from the fine image data S23 including the signal component and the scatter component, the rough image data S21 including the scatter component is converted to high resolution image data such as the image data S23, the fine converted image data S21 including the scatter component is removed from the image data 23 including the signal component and the scatter component. Thereby, the fine image data that mainly has the signal component is created. When the image data S23 where the scatter component is removed by subtraction is spatially corrected, the data corresponding to the specific pixels is interpolated. In this way, the frame rate can be improved, the influence caused by the read out operation of the scatter component to the cycle time can be reduced, and the gap for imaging time between the F-side and the L-side can be shortened.

Figure 14:
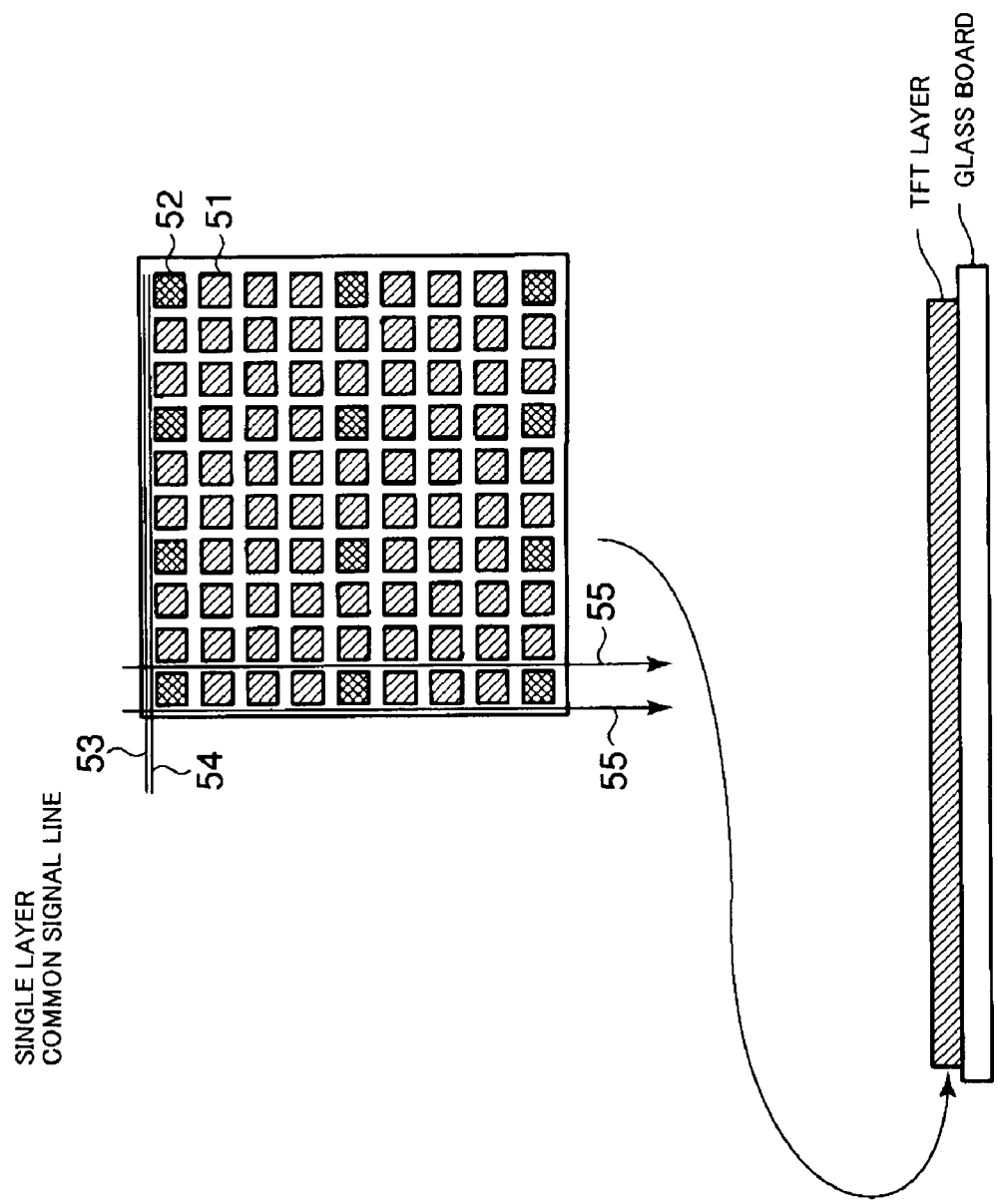
FIG. 14 is an illustration for explaining an example of a one-layer (common signal line) type X-ray detector of FIG. 4.

(1-3) Electric charge read out format+Partial read out type (a single layer, common signal line)+Spatial correction As shown in FIG. 14, the signal lines 55 may be commonly used for the specific pixel and other pixels in the partial read out type. The gate line 54 of the specific pixel 52 is independent from other gate lines 53 of other pixels 51. Since the image processing for subtraction is the same as or similar to what is explained in (1-2), the explanation is omitted. Through this configuration, the frame rate can be improved, the influence caused by the read out operation of the scatter component to the cycle time can be reduced, and the gap for imaging time between the F-side and the L-side can be shortened.

Figure 15:
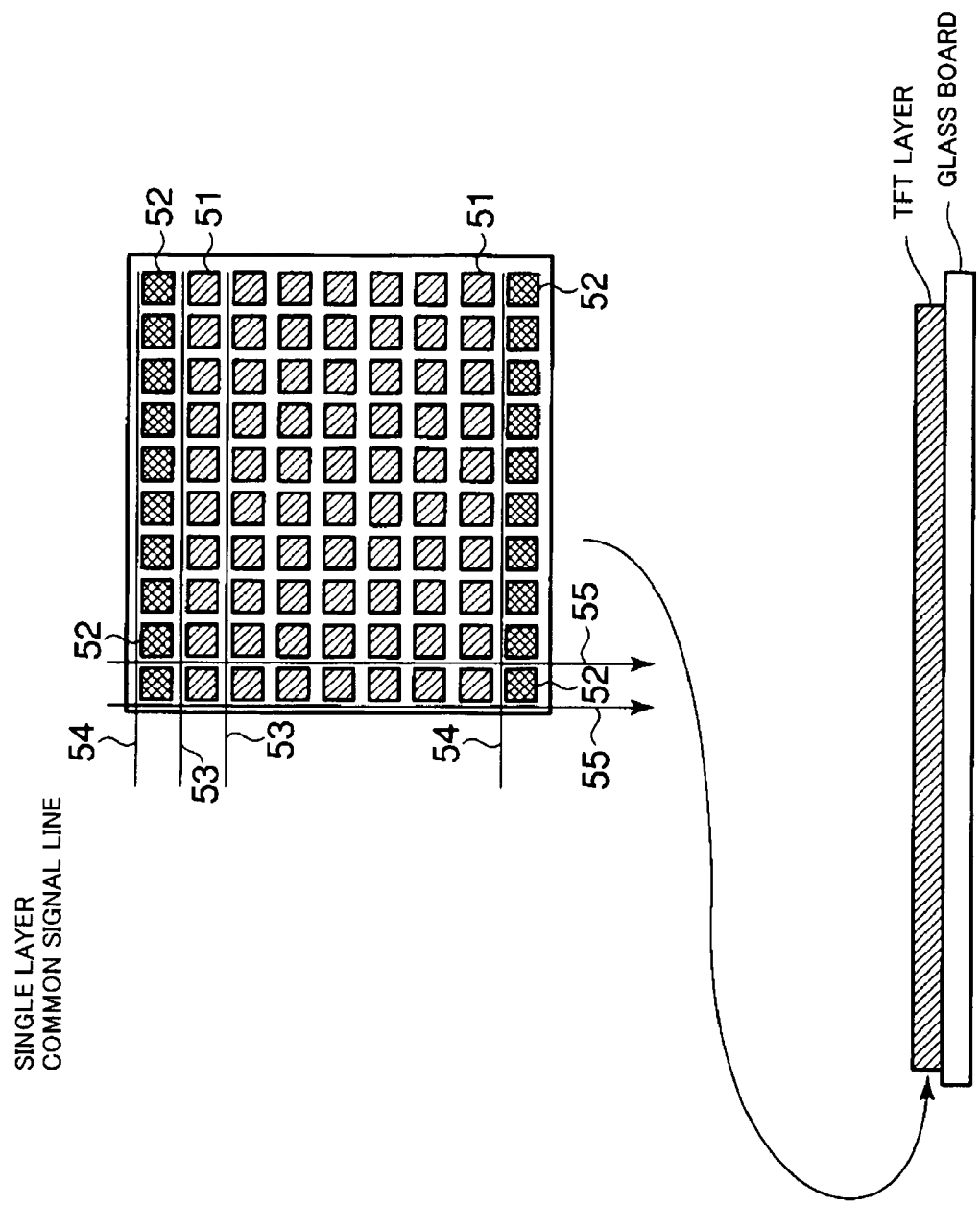
FIG. 15 is an illustration for explaining another example of a one-layer (common signal line) type X-ray detector of FIG. 4.

In addition, in type (1-3) as shown in FIG. 15, the specific pixel 52 may be adapted per line. Specific gate lines 54 separated in the lengthwise direction by predetermined gate lines 53 are adapted. Several pixels connected to the specific gate line 54 and located on the same line are used as the specific pixels when the rough image data is read out. The rough pixel data S11, S12, S21, and S22 are read out when the specific gate lines 54 are driven in order. The data is read out from the all signal lines 55 during the driving of the specific gate lines 54. In this type, the conventional composition of the X-ray detector can be used.

Figure 16:
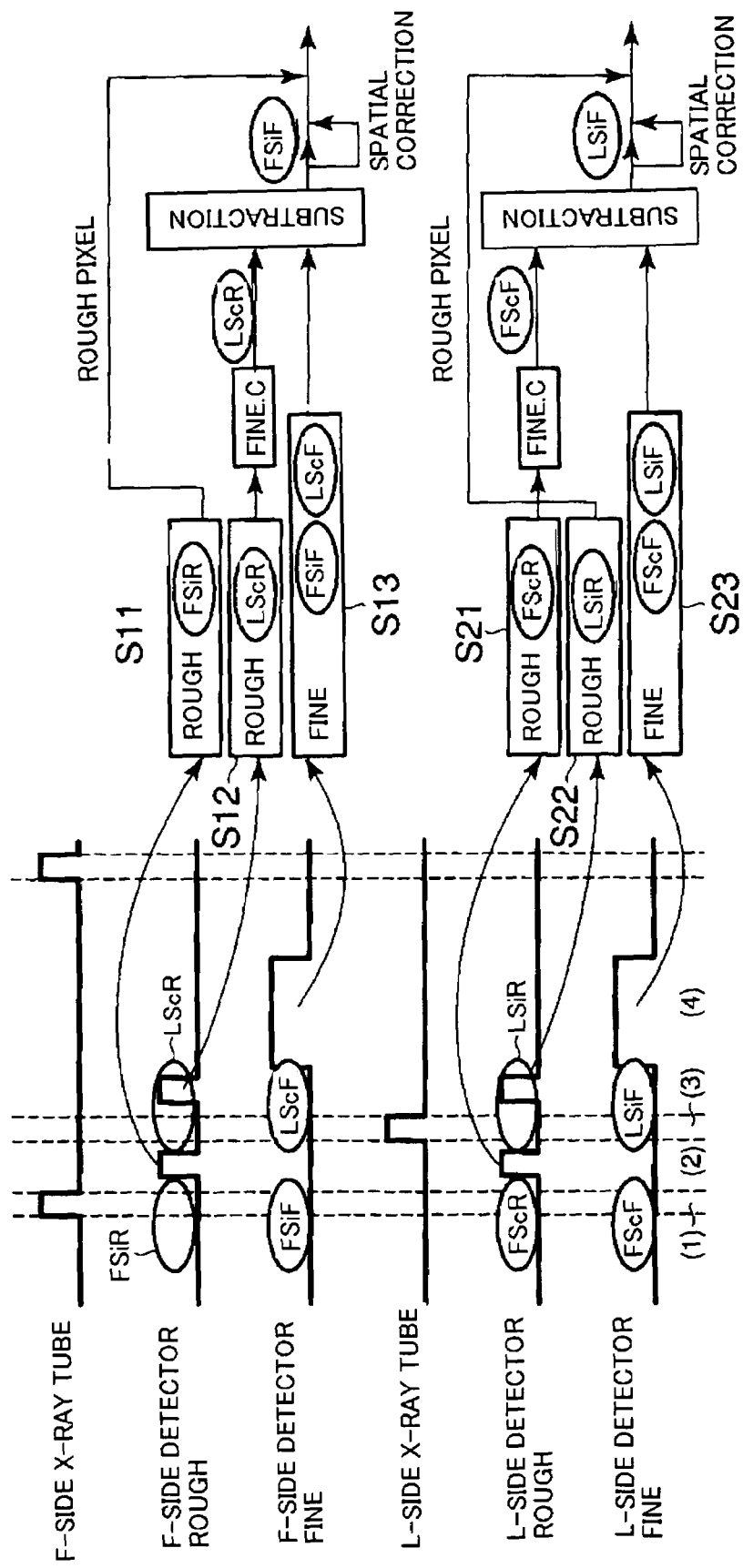
FIG. 16 is an illustration for explaining an imaging sequence and an image processing of each format.

(2-1) Electric charge read out format+Partial read out type (a single layer, independent signal line)+Reuse reconstruction This type is different from (1-2) mainly with respect to the image processing. In (1-2), the data of the specific pixels that cause the signal lack is interpolated by using the spatial correction. On the other hand, as shown in FIG. 16, the data of the specific pixels that cause the signal lack in the fine image data S13 and S23 where the scatter component is removed by the subtraction, is interpolated by the rough image data S11 that includes the signal component and that is read out from the specific pixels of the F-side X-ray detector 12 in term (2). Regarding the L-side, the rough image data S22 that mainly includes the signal component and that is read out from the specific pixels 52 of the L-side X-ray detector 22 in term (4) is used for the interpolation. Since the image data S11 mainly includes the signal component by the direct X-rays from the F-side and includes little scatter component, the fine image data mainly including the signal component can be obtained.

(2-2) Electric charge read out format+Partial read out type (a single layer, common signal line)+Reuse reconstruction This type is different from type (1-3) mainly in terms of image processing. In this image processing, the data of the specific pixels that cause the signal lack in the fine image data S13 and S23 where the scatter component is removed by subtraction, is interpolated by the rough image data S11 that mainly includes the signal component and is read from the specific pixel 52 of the F-side X-ray detector 12 in term (2). Regarding the L-side, the rough image data S22 that mainly includes the signal component and read out from the specific pixels 52 of the L-side X-ray detector 22 in term (4) is used for the interpolation.

(3-1) Voltage read out format+Flush every read out type+ Two layer type

Figure 17:
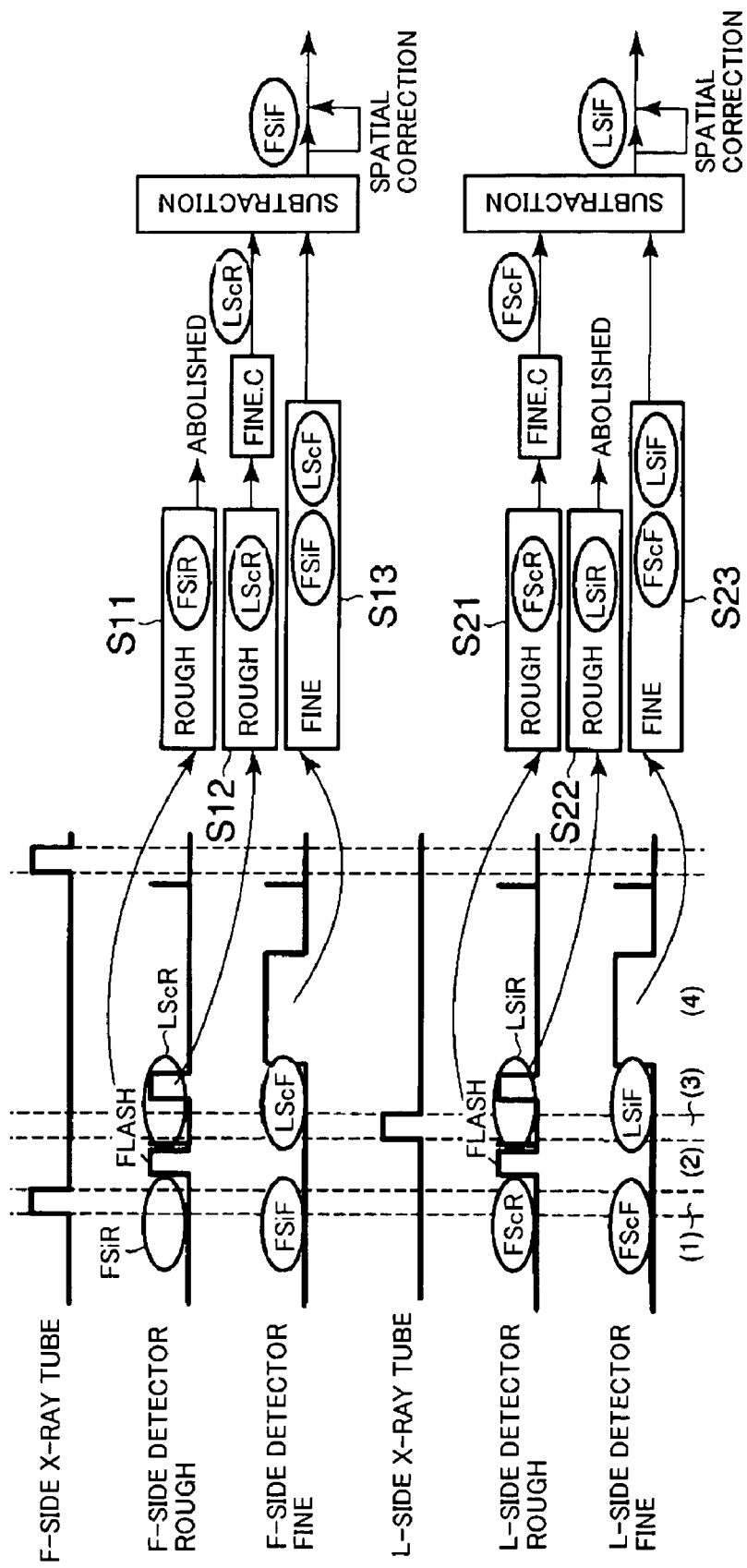
FIG. 17 is an illustration for explaining another imaging sequence and another image processing of each format.

Unlike the electric charge read out format, in the voltage read out format, an electric charge is held in the pixel capacitor even after the read out. Therefore, after the rough image data S12 is read out from the second layer of the F-side X-ray detector 12 in term (2) and before the X-rays are irradiated from the L-side in term (3), as shown in FIG. 17, a flush operation that resets the electric charge of the pixel capacitor of the second layer is performed. By the reset, mixing of the signal component with the image data S12 can be reduced, and the scatter component can be enhanced.

Similarly, the flush operation that resets the electric charge of the pixel capacitor of the second layer is performed after the rough image data S22 is read out from the second layer of the L-side X-ray detector 22 in term (2) and before the X-rays are irradiated from the L-side in term (3). By the reset, mixing of the scatter component with image data S22 can be reduced, and the signal component can be enhanced. Moreover, after the image data S12 and S13 is read out from the first and second layers of the F-side X-ray detector 12 in term (4) and before the X-rays are irradiated from the F-side in the following cycle, the operation that resets the electric charge of the pixel capacitor of the first layer and the second layer is performed. By this reset, the carry-over of the electric charge to the following cycle can be reduced. Similarly, after the image data S22 and S23 is read out from the first and second layers of the L-side X-ray detector 22 in term (4) and before the X-rays are irradiated from the L-side in the following cycle, the operation that resets the electric charge of the pixel capacitor of the first layer and the second layer is performed. By this reset, the carry-over of the electric charge to the following cycle can be reduced. The image processing is the same as or similar to (1-1).

(3-2) Voltage read out format+Flush every read out type+ Partial read out type (a single layer, independent signal line)+Spatial correction Although the flush operation is performed in the above-mentioned voltage read out format, it is similar to a case where the electric charge read out format of (1-2) is changed to the voltage read out format. In this case, on the F-side, the pixel capacitor of the specific pixel 52 is reset in term (2) after the read out of the image data S11. All pixel capacitors including the specific pixel 52 and other pixels 51 are reset after the read out of the image data S12 and S13 in term (4). Similarly, the pixel capacitor of the specific pixel 52 of the L-side is also reset after the read out of the image data S21 in the term (2), and all pixels including the specific pixel 52 and other pixels 51 are reset after the read out of the image data S22 and S23 in term (4). The image processing is similar to the image processing of (1-2). On the F-side, the data corresponding to the specific pixels 52 that cause the signal lack in the image data S13 where the scatter component is removed by subtraction, is interpolated using the spatial correction. Similarly, on the L-side, the data corresponding to the specific pixels 52 that cause the signal lack in the image data S23 where the scatter component is removed by subtraction, is interpolated using the spatial correction.

(3-3) Voltage read out format+Flush every read out type+ Partial read out type (a single layer, common signal line)+ Spatial correction When the voltage read out format is used instead of the electric charge read out format of (1-3), since the electric charge is held, the flush is also performed. On the F-side, the pixel capacitors of the specific pixels 52 are reset after the image data S11 is read out in term (2), and the pixel capacitors of all pixels including the specific pixels and the other pixels are also reset, after the image data S12 and S13 is read out in term (4). On the L-side, the pixel capacitors of the specific pixels 52 are reset after the image data S21 is read out in term (2), and also the pixel capacitors of all pixels including the specific pixels and the other pixels are reset, after the image data S22 and S23 is read out in term (4).

The image processing is the same as or similar to what is explained in (1-3). Regarding the F-side, the data corresponding to the specific pixels 52 is spatially interpolated. Similarly, regarding the L-side, the data corresponding to the specific pixels is spatially interpolated.

Figure 18:
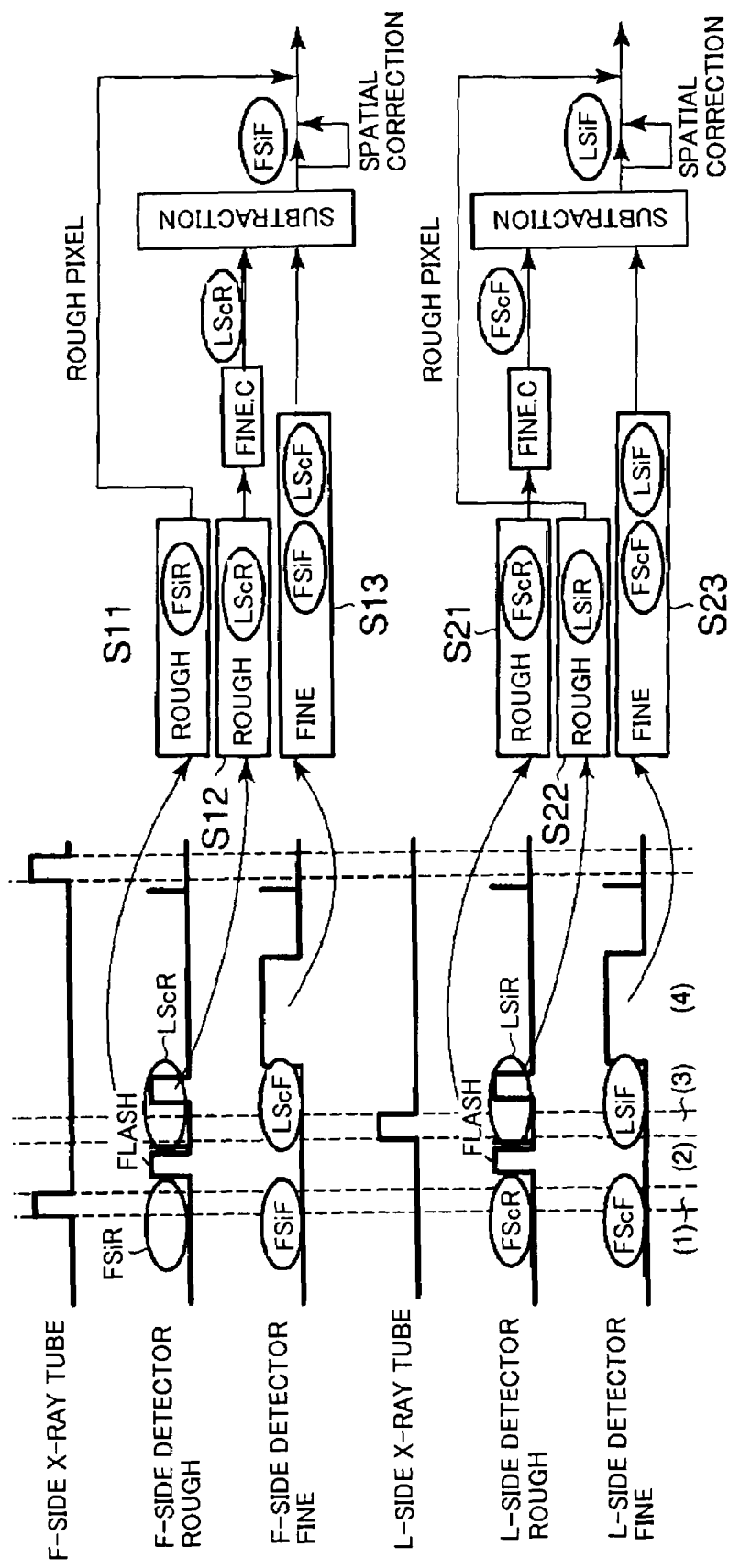
FIG. 18 is an illustration for explaining another imaging sequence and another image processing of each format.

(4-1) Voltage read out format+Flush every read out type+ Partial read out type (a single layer, independent signal line)+Reuse reconstruction This type is different from (3-2) mainly with respect to the image processing. As shown in FIG. 18, the image processing is performed by a reuse reconstruction instead of spatial correction. On the F-side, the data of the specific pixels that cause the signal lack in the fine image data S13 and S23 where the scatter component is removed by subtraction, is interpolated by the rough image data S11 that includes the signal component read out from the specific pixels of the F-side X-ray detector 12 in term (2). Regarding the L-side, the rough image data S22 that mainly includes the signal component read out from the specific pixels 52 of the L-side X-ray detector 22 in term (4) is used for the interpolation.

(4-2) Voltage read out format+Flush every read out type+ Partial read out type (a single layer, common signal line)+ Reuse reconstruction This type is different from (3-3) mainly with regard to the image processing. As shown in FIG. 18, the image processing is performed by reuse reconstruction instead of spatial correction. On the F-side, the data of the specific pixels that cause the signal lack in the fine image data S13 and S23 where the scatter component is removed by subtraction is interpolated by the rough image data S11 that includes the signal component read out from the specific pixels of the F-side X-ray detector 12 in term (2). Regarding the L-side, the rough image data S22 that mainly includes the signal component read out from the specific pixels 52 of the L-side X-ray detector 22 in term (4) is used for the interpolation.

(5-1) Voltage read out format+Flush every frame type+ Two layer type

Figure 19:
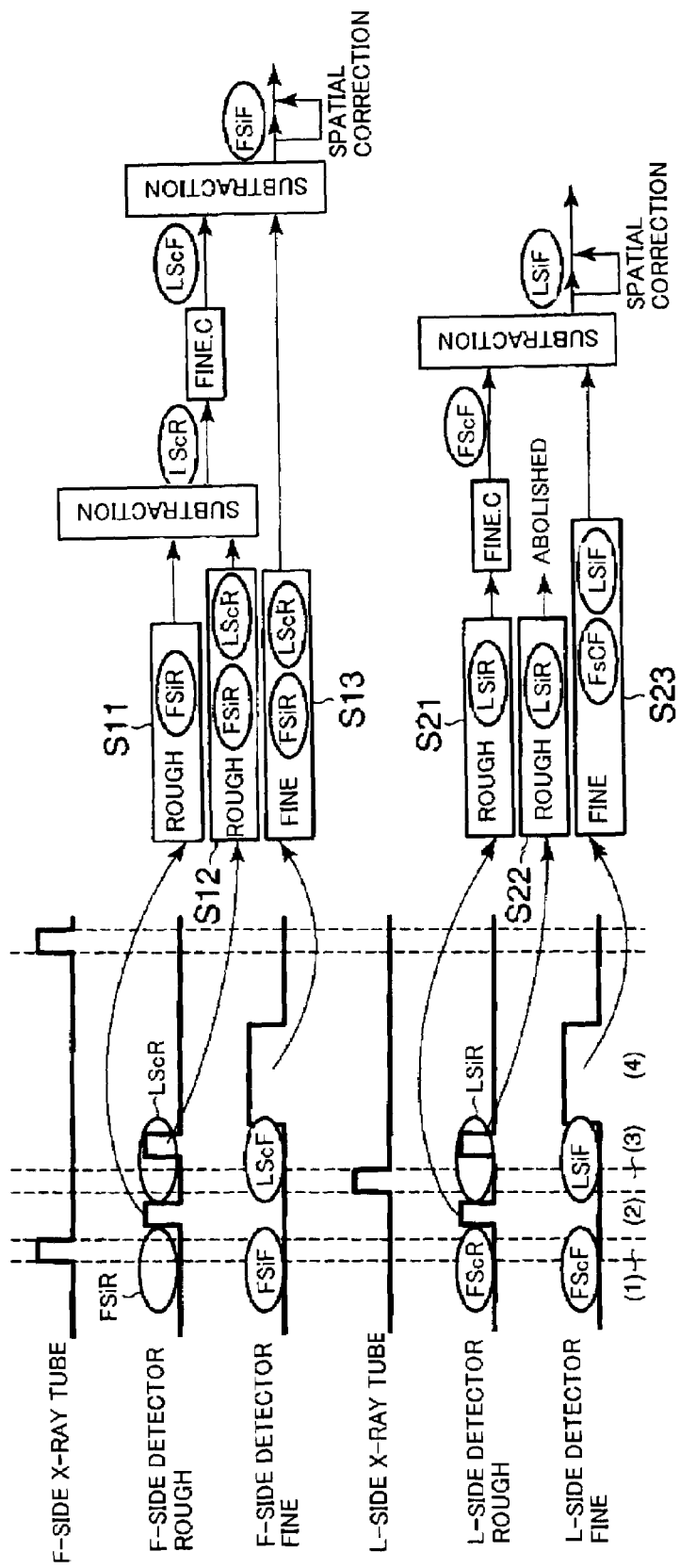
FIG. 19 is an illustration for explaining another imaging sequence and another image processing of each format.
Figure 20:
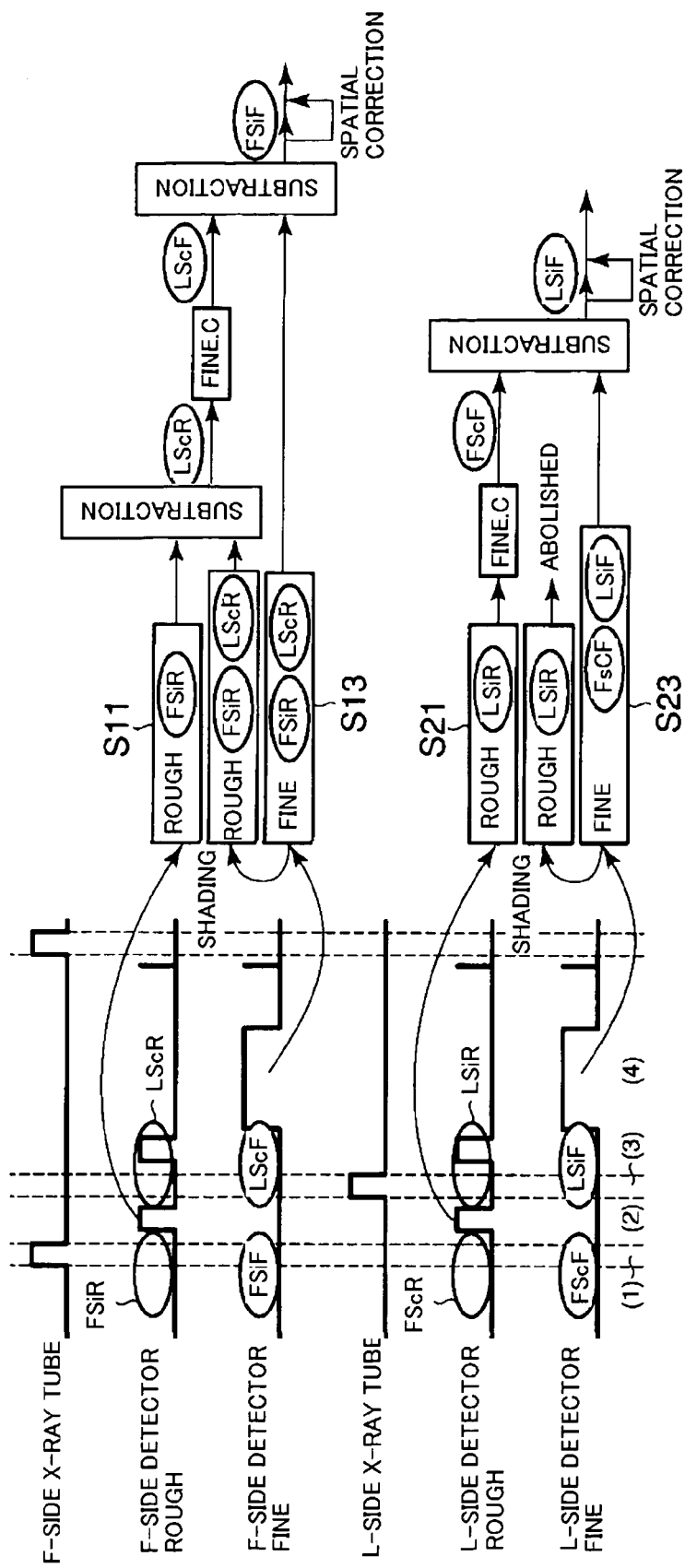
FIG. 20 is an illustration for explaining another imaging sequence and another image processing of each format.
Figure 21:
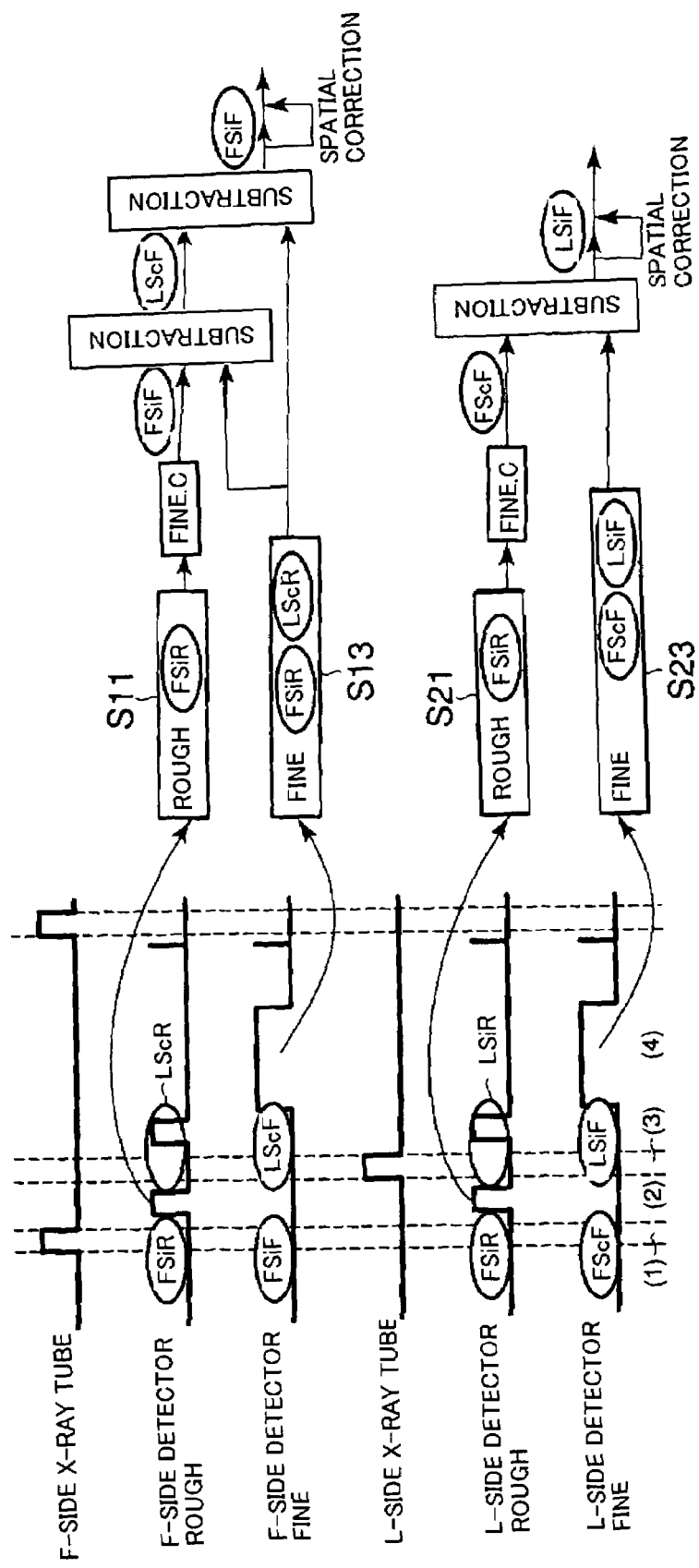
FIG. 21 is an illustration for explaining another imaging sequence and another image processing of each format.
Figure 22:
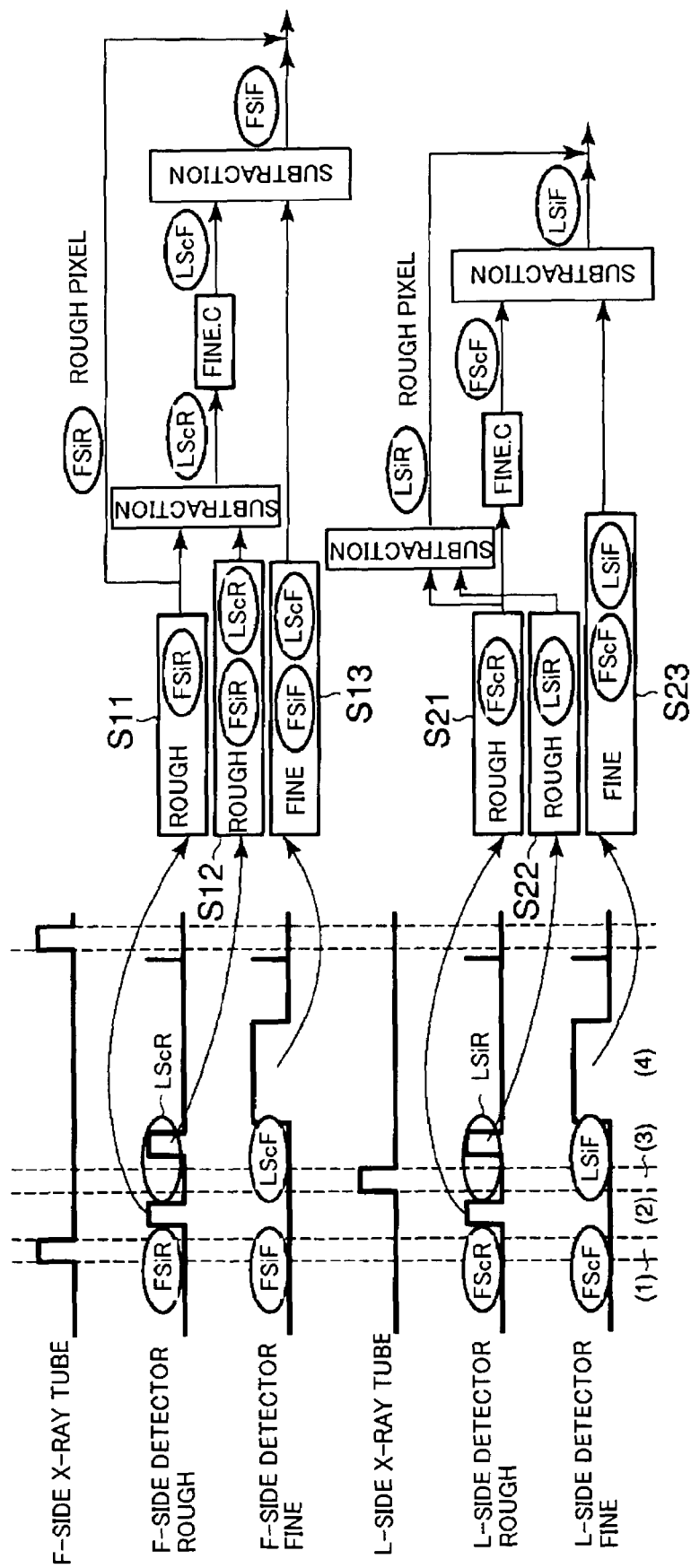
FIG. 22 is an illustration for explaining another imaging sequence and another image processing of each format.
Figure 23:
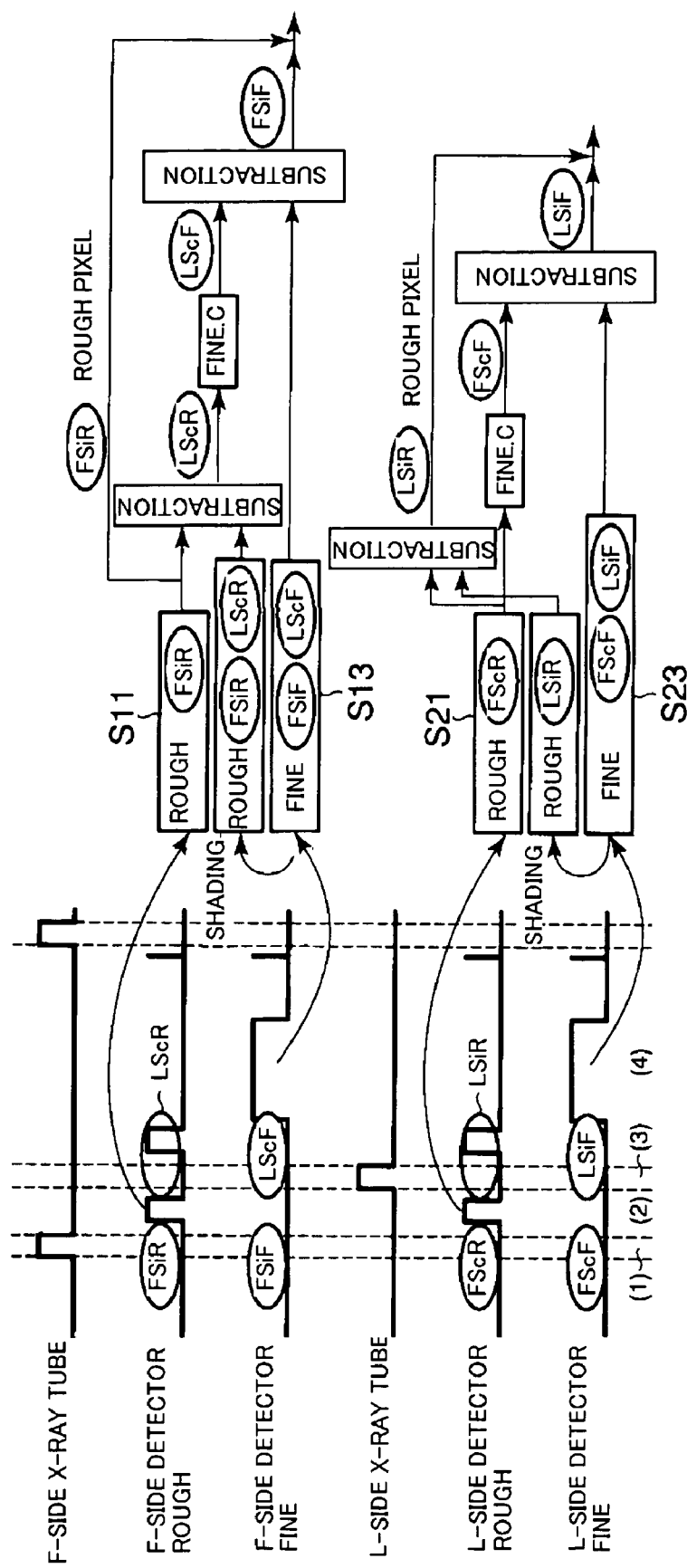
FIG. 23 is an illustration for explaining another imaging sequence and another image-processing of each format.
Figure 24:
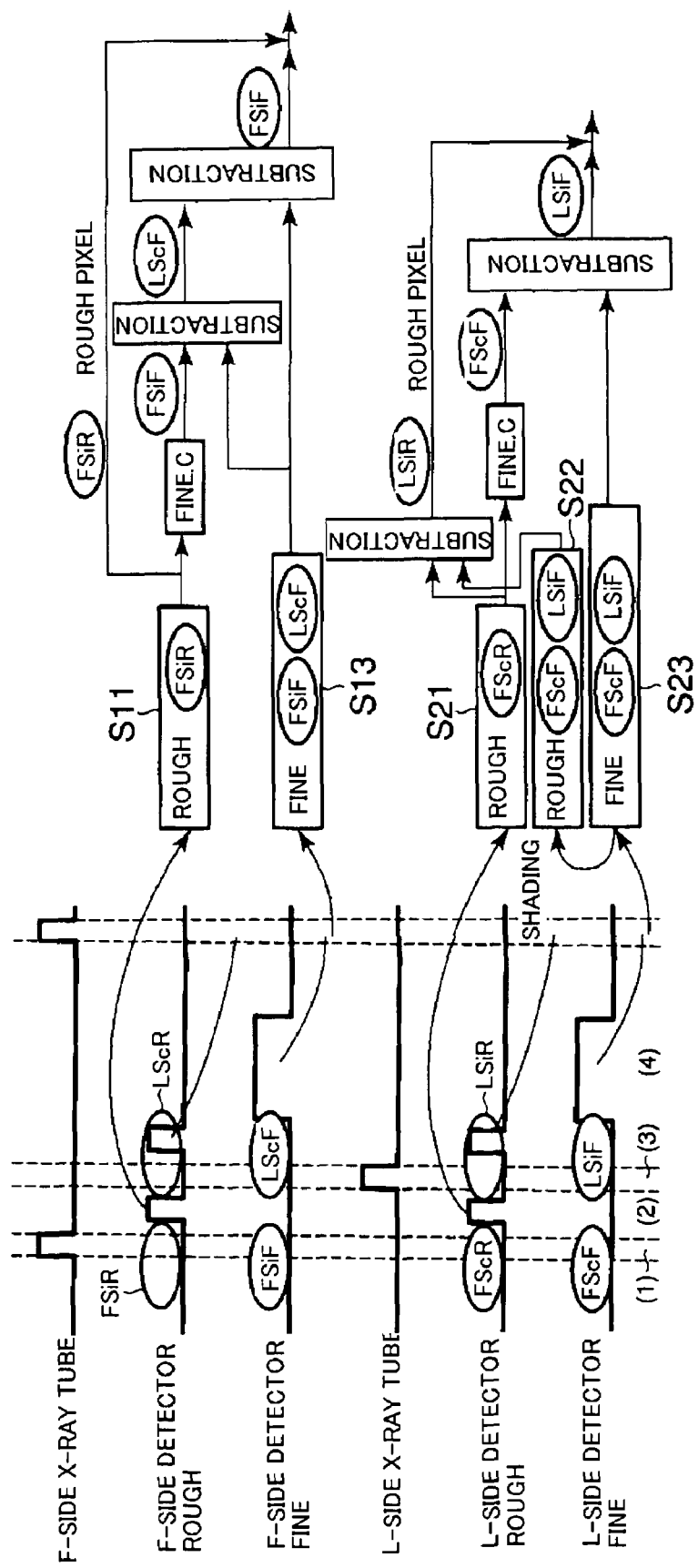
FIG. 24 is an illustration for explaining another imaging sequence and another image processing of each format.

This type is different from (3-1) mainly with respect to the image processing and the timing of the flush operation. The timing of the flush operation is shown in FIG. 19, which shows that the electric charge of the pixel capacitor of the second layer of the F-side and the L-side X-ray detectors 12 and 22 is not reset in term (2). After the image data S12 and S13 is read out from the first and second layers of the F-side X-ray detector 12 in term (4) and before the X-rays are irradiated from the F-side in the following cycle, the operation that resets the electric charge of the pixel capacitor of the first layer and the second layer is performed. Similarly, after the image data S22 and S23 is read out from the first and second layers of the L-side X-ray detector 22 in term (4) and before the X-rays are irradiated from the L-side in the following cycle, the operation that resets the electric charge of the pixel capacitor of the first layer and the second layer is performed.

Since the electric charge of the pixel capacitor of the second layer of the F-side and the L-side X-ray detectors 12 and 22 in term (2), the rough image data S12 and S22 read out in term (4) includes the signal component and the scatter component. To remove the signal component from the image data S12 to obtain the scatter component, the image data S11 mainly including the signal component is subtracted from the image data S12 including both the signal component and the scatter component. The fine image data that is converted from the image data S12 mainly including the scatter component is subtracted from the fine image data S13 including both the signal component and the scatter component to obtain the fine image data that includes almost none of the scatter component. The image processing for the L-side is the same as or similar to (3-1).

(5-2) Voltage read out format+Flush every frame type+ Partial read out type (a single layer, independent signal line)+Spatial correction This type is different from (3-2) mainly with regard to image processing and timing of the flush operation. As flush shown in FIG. 19, the electric charge of the pixel capacitor of the second layer of the F-side and L-side X-ray detectors 12 and 22 is not reset in term (2). To remove the signal component from the image data S12 and to obtain the scatter component, the image data S11 mainly including the signal component is subtracted from the image data S12 including both the signal component and the scatter component. The fine image data that is converted from the image data S12 mainly including the scatter component is subtracted from the fine image data S13 including both the signal component and the scatter component to obtain the fine image data that includes almost none of the scatter component. When the spatial correction is performed to the fine image data S13 that does not include the scatter component, the data corresponding to the specific pixel is interpolated. The image processing for the L-side is the same as or similar to (3-2).

(5-3) Voltage read out format+Flush every frame type+ Partial read out type (a single layer, common signal line)+ Spatial correction This type is different from (3-3) mainly with respect to image processing and timing of the flush operation. As flush shown in FIG. 19, the electric charge of the pixel capacitor of the second layer of the F-side and L-side X-ray detectors 12 and 22 is not reset in term (2). To remove the signal component from the image data S12 and to obtain the scatter component, the image data S11 mainly including the signal component is subtracted from the image data S12 including both the signal component and the scatter component. The fine image data that is converted from the image data S12 mainly including the scatter component is subtracted from the fine image data S13 including both the signal component and the scatter component to obtain the fine image data that includes almost none of the scatter component. When the spatial correction is performed to the fine image data S13 that does not include the scatter component, the data corresponding to the specific pixel is interpolated. The image processing to the L-side is the same as or similar to (3-3).

(6-1) Voltage read out format+Flush every frame type+ Two layer type+Low resolution conversion This type is different from (5-1) mainly with regard to the image processing. In (5-1), when the image data S11 mainly including the signal component is subtracted from the image data S12 including the signal component and the scatter component, the image data that mainly includes the scatter component but includes almost none of the signal component is created. On the other hand, in (6-1), the resolution of the image data S13 including the signal component and the scatter component is reduced (by low resolution conversion) as much as the rough image data S11 by a pixel skipping calculation or a local average calculation. When the rough image data mainly including the signal component is subtracted from the rough image data converted by low resolution conversion, the rough image data 13 mainly including the scatter component is created. The rough image data 13 is converted to the fine image data, and the fine image data 13 is subtracted from the fine image data. Thereby, the fine image data that includes almost none of the scatter component is created. The image processing for the L-side is the same as or similar to (5-1).

(6-2) Voltage read out format+Flush every frame type+ Partial read out type (a single layer, independent signal line)+Spatial correction+Low resolution conversion This type is different from the type of the above (5-2) mainly regarding image processing. In (6-2) as well as in (6-1), the resolution of the image data S113 including the signal component and the scatter component is reduced as much as the rough image data S11 by a pixel skipping calculation or a local average calculation. When the rough image data mainly including the signal component is subtracted from the rough image data converted by low resolution conversion, the rough image data S13 mainly including the scatter component is created. The rough image data S13 mainly including the scatter component is converted to the fine image data S13, and the fine image data S13 is subtracted from the non-converted original fine image data S13. Thereby, the fine image data S13 that does not almost include the scatter component is created. The image processing for the L-side is the same as or similar to the (5-2).

(6-3) Voltage read out format+Flush every frame type+ Partial read out type (a single layer, common signal line)+ Spatial correction+Low resolution conversion This type is different from (5-3) mainly with regard to the image processing. In (6-3) as well as (6-1), the resolution of the image data S13 including the signal component and the scatter component is reduced as much as the rough image data S11 by a pixel skipping calculation or a local average calculation. When the rough image data S11 mainly including the signal component is subtracted from the rough image data S13 converted by low resolution conversion, the rough image data S13 mainly including the scatter component is created. The rough image data S13 is converted to the fine image, and the fine image data S13 is subtracted from the fine image data S13. Thereby, the fine image data S13 that includes almost none of the scatter component is created. The image processing to the L-side is the same as or similar to the (5-3).

(7-1) Voltage read out format+Flush every frame type+ Two layer type+Low resolution conversion of modified algorithm This type is different from (6-1) mainly with respect to the algorithm of the low resolution conversion. In (7-1), the rough image data S11 mainly including the signal component is converted to the fine image data, and the fine image data is subtracted from the fine image data S13 including both the signal image data and the scatter data. The fine image data S13 mainly including the scatter component is created, and the fine image data S13 mainly including the scatter component is subtracted from the fine image data S13.

(7-2) Voltage read out format+Flush every frame type+ Partial read out type (a single layer, independent signal line)+Spatial correction+Low resolution conversion of modified algorithm This type is different from (6-2) mainly with respect to the algorithm for low resolution conversion. The order between the fine conversion and the subtraction is reversed in comparison with (6-2). In (7-2), after the rough image data S11 mainly including the signal component is converted to the fine image data, the converted image data is subtracted from the fine image data S13 including the signal component and the scatter component. Thereby, the created fine image data S13 mainly including the scatter component is subtracted from the fine image data S13.

(7-3) Voltage read out format+Flush every frame type+ Partial read out type (a single layer, common signal line)+ Spatial correction+Low resolution conversion of modified algorithm This type is different from (6-3) mainly regarding low resolution conversion algorithm. The order between the fine conversion and the subtraction is reversed in comparison with (6-3). In (7-3), after the rough image data S11 mainly including the signal component is converted to the fine image, the converted image data is subtracted from the fine image data S13 including the signal component and the scatter component. Thereby, the created fine image data S13 mainly including the scatter component is subtracted from the fine image data S13.

(8-1) Voltage read out format+Flush every frame type+ Partial read out type (a single layer, independent signal line)+Reuse reconstruction This type uses the reuse reconstruction instead of the spatial correction used in (5-2). In (5-2), the spatial correction is performed to the image data S13 that includes almost none of the scatter component by subtraction, and the data corresponding to the specific pixels is interpolated. In (8-1), the data corresponding to the specific pixels on the image data S13 that includes almost none of the scatter component is interpolated by the rough image data S11 that mainly includes the signal component that is read out in term (2).

Regarding the L-side, the rough image data S21 that mainly includes the scatter component read out in term (2) is subtracted from the rough image data S22 that includes the signal component and the scatter component that is read out in term (4). Thereby, the rough image data for interpolation mainly including the signal component is created. By using the created imaged data mainly including the signal component, the data corresponding to the specific pixels on the fine image data S23 that includes almost none of the scatter component is interpolated.

(8-2) Voltage read out format+Flush every frame type+ Partial read out type (a single layer, common signal line)+ Reuse reconstruction In this type, reuse reconstruction is used instead of spatial correction, which is different from (5-3). In (5-3), the lacked data corresponding to the specific pixel is interpolated with the spatial correction of the fine image data that includes almost none of the scatter component and that is created by subtraction. In (8-2), the data corresponding to the specific pixels on the image data S13 that includes almost none of the scatter component and that is created by subtraction is interpolated by the image data S11 that mainly includes signal component read out in term (2).

Regarding the L-side, the rough image data S21 that mainly includes the scatter component read out in term (2) is subtracted from the rough image data S22 that includes the signal component and the scatter component read out in term (4). Thereby, the rough image data for interpolation mainly including the signal component is created. By using the created imaged data mainly including the signal component, the data corresponding to the specific pixels on the fine image data S23 that includes almost none of the scatter component is interpolated.

(9-1) Voltage read out format+Flush every frame type+ Partial read out type (a single layer, independent signal line)+Reuse reconstruction+Low resolution conversion This type is different from (8-1) mainly about the following point. In (8-1), to create the fine image data mainly including the scatter component to be subtracted from the fine image data S13 including the signal component and the scatter component, the rough image data mainly including the scatter component is created by subtracting the rough image data S11 mainly including the signal component in term (2) from the rough image data S12 including the signal component and the scatter component in term (4). In (9-1), the fine image data S13 including the signal component and the scatter component in term (4) is converted to rough image data S13 by low resolution conversion, and the rough image data S11 mainly including the signal component in term (2) is subtracted from the created rough image data S13 by conversion. Thereby, the fine image data is created mainly including the scatter component to be subtracted from the fine image data S13 including the signal component and the scatter component.

Similarly, regarding the L-side, the fine image data S23 including the signal component and the scatter component in term (4) is converted to rough image data by low resolution conversion, and the rough image data S21 mainly including the signal component in term (2) is subtracted from the rough image data S23. Thereby, the fine image data is created mainly including the scatter component to be subtracted from the fine image data S23 including the signal component and the scatter component.

(9-2) Voltage read out format+Flush every frame type+ Partial read out type (a single layer, common signal line)+ Reuse reconstruction+Low resolution conversion This type is different from (8-2) mainly about the following point. In (8-2), to create the fine image data mainly including the scatter component to be subtracted from the fine image data S13 including the signal component and the scatter component, the rough image data mainly including the scatter component is created by subtracting the rough image data S11 mainly including the signal component in term (2) from the rough image data S12 including the signal component and the scatter component in term (4). In (9-2), the fine image data S13 including the signal component and the scatter component in term (4) is converted to rough image data by low resolution conversion, and the rough image data S11 mainly including the signal component in term (2) is subtracted from the rough image data S13. Thereby, fine image data is created mainly including the scatter component to be subtracted from the fine image data S13 including the signal component and the scatter component.

Similarly, regarding the L-side, the fine image data S23 including the signal component and the scatter component in term (4) is converted to rough image data by low resolution conversion, and the rough image data S21 mainly including the signal component in term (2) is subtracted from the rough image data S23. Thereby, the fine image data is created mainly including the scatter component to be subtracted from the fine image data S23 including the signal component and the scatter component.

(10-1) Voltage read out format+Flush every frame type+ Partial read out type (a single layer, independent signal line)+Reuse reconstruction+Low resolution conversion of modified algorithm In (9-1), the fine image data S13 including the signal component and the scatter component in term (4) is converted to rough image data by low resolution conversion, and the rough image data S11 mainly including the signal component in term (2) is subtracted from the created rough image data S13 by conversion. Thereby, fine image data is created mainly including the scatter component to be subtracted from the fine image data S13 including the signal component and the scatter component. In (10-1), the rough image data S11 mainly including the signal component in term (2) is converted to fine image data, and the created fine image data mainly including the signal component is subtracted from the fine image data S13 including the signal component and the scatter component in term (4). Thereby, the fine image data mainly including the scatter component to be subtracted from the fine image data S13 including the signal component and the scatter component is created.

Similarly, regarding the L-side, the rough image data S21 mainly including the signal component in term (2) is converted to fine image data, and the created fine image data mainly including the signal component is subtracted from the fine image data S23 including the signal component and the scatter component in term (4). Thereby, the fine image data mainly including the scatter component to be subtracted from the fine image data including the signal component and the scatter component in term (4).

(10-2) Voltage read out format+Flush every frame type+ Partial read out type (a single layer, common signal line)+ Reuse reconstruction+Low resolution conversion of modified algorithm This type is different from (9-2) mainly about the following point. In (9-2), the fine image data S13 including the signal component and the scatter component in term (4) is converted to rough image data by low resolution conversion, and the rough image data S11 mainly including the signal component in term (2) is subtracted from the rough image data S13. Thereby, fine image data is created mainly including the scatter component to be subtracted from the fine image data S13 including the signal component and the scatter component.

By contrast, in (10-2), the rough image data S11 mainly including the signal component in term (2) is converted to the fine image, and the fine image data is subtracted from the fine image data S13 including the signal component and the scatter component in term (4). Thereby, the fine image data mainly including the scatter component is to be subtracted from the fine image data S13 including the signal component and the scatter component in term (4).

Similarly, regarding the L-side, the rough image data S21 mainly including the signal component in term (2) is converted to fine image data, and the fine image data is subtracted from the fine image data S23 including the signal component and the scatter component in term (4). Thereby, the fine image data mainly including the scatter component is to be subtracted from the fine image data S23 including the signal component and the scatter component in term (4).

In at least one of the above embodiments of the X-ray diagnosis apparatus for obtaining at least two X-ray images from respective directions, the influence of the scatter X-rays is reduced or the frame rate is improved.

The present invention may be not limited to the above embodiments, and various modifications may be made without departing from the spirit or scope of the general inventive concept. It is therefore to be understood that within the scope of the appended claims, the present invention may be practiced differently than as specifically described herein. Although the above embodiment and modification may include various steps or various elements, one or more steps or elements may be arbitrarily selected. For instance, one or more steps or elements described as the embodiment or modification may be omitted.

For example, the X-ray detector may be a direct change type X-ray detector that directly changes an incident X-rays into an electric charge, or an indirect change type that changes an incident X-rays into an optical signal and changes the optical signal to an electric charge. In the above, it is explained that a solid flat detector that includes TFT is used as the X-ray detectors, however other detector, such as a semiconductor-type detector or a gas-type detector may be used. One of semiconductor-type detectors includes arranged detection elements using FET and Si, for example. One of gas-type detectors uses a gas that is located in a sealed box, such as an ionization chamber, in order to change X-rays to electric charges.

The invention claimed is:

1. A method for obtaining an X-ray image using an X-ray diagnosis apparatus including a first imaging system including a first X-ray tube and a first X-ray detector and a second imaging system including a second X-ray tube and a second X-ray detector, the method comprising:
    collecting scatter data using the second X-ray detector after at least one X-ray is irradiated from the first X-ray tube;
    collecting scatter data using the first X-ray detector after at least one X-ray is irradiated from the second X-ray tube and subsequently collecting the scatter data using the second X-ray detector;
    collecting, substantially simultaneously, image data including a scatter component using the first and the second X-ray detectors; and
    obtaining X-ray images imaged using the first imaging system and the second imaging system by subtracting the scatter data collected by the first and second X-ray detectors from the image data including the scatter component collected by the first and second X-ray detectors,
    wherein a collection time of the scatter data is shorter than a collection time of the image data including the scatter component.

2. A method for obtaining an X-ray image using an X-ray diagnosis apparatus including a first imaging system including a first X-ray tube and a first X-ray detector and a second imaging system including a second X-ray tube and a second X-ray detector, the method comprising:
  collecting, substantially simultaneously, scatter data using the first and second X-ray detectors after at least one X-ray is irradiated from the first X-ray tube;
  collecting, substantially simultaneously, image data including a scatter component using the first and the second X-ray detectors after at least one X-ray is irradiated from the second X-ray tube; and
  obtaining X-ray images imaged using the first imaging system and the second imaging system by subtracting the scatter data collected by the first and second X-ray detectors from the image data including the scatter component collected by the first and second X-ray detectors,
  wherein a collection time of the scatter data is shorter than a collection time of the image data including the scatter component.

3. A method for obtaining an X-ray image using an X-ray diagnosis apparatus including a first imaging system including a first X-ray tube and a first X-ray detector and a second imaging system including a second X-ray tube and a second X-ray detector, the method comprising:
  collecting, substantially simultaneously, first scatter data using the first and second X-ray detectors after at least one X-ray is irradiated from the first X-ray tube;
  collecting second scatter data using the first X-ray detector after at least one X-ray is irradiated from the second X-ray tube and subsequently collecting the second scatter data using the second X-ray detector,
  subsequently collecting, substantially simultaneously, image data including a scatter component using the first and second X-ray detectors;
  subtracting the second scatter data from the first scatter data, thereby obtaining subtracted scatter data;
  obtaining an X-ray image by subtracting the subtracted scatter data from the image data including the scatter component collected by the first X-ray detector; and
  obtaining an X-ray image by subtracting the scatter data collected by the second X-ray detector from the image data including the scatter component collected by the second X-ray detector,
  wherein a collection time of the scatter data is shorter than a collection time of the image data including the scatter component.

4. A method for obtaining X-ray image by an X-ray diagnosis apparatus including a first X-ray tube configured to irradiate X-rays in a first direction, a first X-ray detector corresponding to the first X-ray tube, a second X-ray tube for irradiating X-rays in a second direction different from the first direction, and a second X-ray detector corresponding to the second X-ray tube, the method comprising:
  collecting first image data using the second X-ray detector based on at least one X-ray irradiated from the first X-ray tube;
  collecting second image data using the first X-ray detector based on at least one X-ray irradiated from the second X-ray tube;
  collecting third image data at a speed lower than a collecting speed of the second image data using the first X-ray detector based on the X-rays irradiated from the first and second X-ray tubes;
  collecting fourth image data at a speed lower than a collecting speed of the first image data using the second X-ray detector, substantially simultaneously with the collecting the third image data, based on the X-rays irradiated from the first and second X-ray tubes;
  removing a scatter component included in the third image data using the second image data; and
  removing a scatter component included in the fourth image data using the first image data.

5. The method for obtaining X-ray image according to claim 4, wherein a spatial resolution of the first image data is lower than a spatial resolution of the fourth image data.

6. The method for obtaining X-ray image according to claim 5, wherein a spatial resolution of the second image data is lower than a spatial resolution of the third image data.

7. The method for obtaining X-ray image according to claim 4, wherein the collection of the fourth image data is subsequent to the collection of the first image data.

8. The method for obtaining X-ray image according to claim 7, wherein the collection of the third image data is subsequent to the collection of the second image data.

9. The method for obtaining X-ray image according to claim 8, further comprising collecting fifth image data using the first X-ray detector substantially simultaneous to collecting the first image.

10. The method for obtaining X-ray image according to claim 9, wherein the removal of the scatter component included in the third image data uses the fifth image data.

11. The method for obtaining X-ray image according to claim 10, further comprising collecting sixth image data using the second X-ray detector substantially simultaneously to collecting the second image.

12. The method for obtaining X-ray image according to claim 11, wherein the removal of the scatter component included in the fourth image data uses the sixth image data.

13. A method for obtaining an X-ray image using an X-ray diagnosis apparatus including a first X-ray tube configured to irradiate X-rays in a first direction, a first X-ray detector corresponding to the first X-ray tube, a second X-ray tube for irradiating X-rays in a second direction different from the first direction, and a second X-ray detector corresponding to the second X-ray tube, the method comprising:
  collecting first image data using the second X-ray detector based on at least one X-ray irradiated from the first X-ray tube;
  collecting second image data using the first X-ray detector based on the at least one X-ray irradiated from the first X-ray tube;
  collecting third image data using the first X-ray detector based on X-rays irradiated from the first and second X-ray tubes;
  collecting fourth image data using the second X-ray detector, substantially simultaneously to collecting the third image data, based on the X-rays irradiated from the first and second X-ray tubes;
  removing a scatter component included in the third image data using the second image data; and
  removing a scatter component included in the fourth image data using the first image data.

14. A method for obtaining an X-ray image using an X-ray diagnosis apparatus including a first X-ray tube configured to irradiate X-rays in a first direction, a first X-ray detector corresponding to the first X-ray tube, a second X-ray tube configured to irradiate X-rays in a second direction different from the first direction, and a second X-ray detector corresponding to the second X-ray tube, the method comprising:
  irradiating at least one X-ray from the first X-ray tube;
  collecting first image data using the second X-ray detector based on the at least one X-ray irradiated from the first X-ray tube;
  irradiating at least one X-ray from the second X-ray tube;

collecting second image data using the second X-ray detector based on the X-rays irradiated from the first and second X-ray tubes at a lower speed than a collecting speed of the first image data; and removing a scatter component included in the second image data using the first image data.

15. An X-ray diagnosis apparatus, comprising:

a first X-ray tube configured to irradiate X-rays in a first direction;

a first X-ray detector corresponding to the first X-ray tube;

a second X-ray tube configured to irradiate X-rays in a second direction different from the first direction;

a second X-ray detector corresponding to the second X-ray tube;

a controller configured to control the second X-ray detector to collect first image data based on at least one X-ray irradiated from the first X-ray tube, the first X-ray detector to collect second image data based on at least one X-ray irradiated from the second X-ray tube, the first X-ray detector to collect third image data based on the X-rays irradiated from the first and second X-ray tubes at a lower speed than a collecting speed of the second image data, the second X-ray detector to collect fourth image data, substantially simultaneously to collecting the third image data, based on the X-rays irradiated from the first and second X-ray tubes at a lower speed than a collecting speed of the first image data; and an image processor configured to remove a scatter component included in the third image data using the second image data and to remove a scatter component included in the fourth image data using the first image data.

16. An X-ray diagnosis apparatus, comprising:

a first X-ray tube configured to irradiate X-rays in a first direction;

a first X-ray detector corresponding to the first X-ray tube;

a second X-ray tube configured to irradiate X-rays in a second direction that is different from the first direction;

a second X-ray detector corresponding to the second X-ray tube;

a controller configured to control the second X-ray detector to collect first image data based on at least one X-ray irradiated from the first X-ray tube, the first X-ray detector to collect second image data based on at least one X-ray irradiated from the first X-ray tube, the first X-ray detector to collect third image data based on the X-rays irradiated from the first and second X-ray tubes, the second X-ray detector to collect fourth image data, substantially simultaneously to collecting the third image data, based on the X-rays irradiated from the first and second X-ray tubes; and an image processor configured to remove a scatter component included in the third image data by using the second image data and to remove a scatter component included in the fourth image data using the first image data.

17. An X-ray diagnosis apparatus, comprising:

a first X-ray tube configured to irradiate X-rays in a first direction;

a first X-ray detector corresponding to the first X-ray tube;

a second X-ray tube configured to irradiate X-rays in a second direction different from the first direction;

a second X-ray detector corresponding to the second X-ray tube;

a controller configured to control the first X-ray tube to irradiate at least one X-ray, the second X-ray detector to collect first image data based on the at least one X-ray irradiated from the first X-ray tube, the second X-ray tube to irradiate at least one X-ray, and the second X-ray detector to collect second image data based on the X-rays irradiated from the first and second X-ray tubes at a lower speed than a collecting speed of the first image data; and an image processor configured to remove a scatter component included in the second image data using the first image data.

* * * * *